United States Patent
Sughrue et al.

(10) Patent No.: US 11,666,266 B2
(45) Date of Patent: Jun. 6, 2023

(54) SOURCE LOCALIZATION OF EEG SIGNALS

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU)

(73) Assignee: Omniscient Neurotechnology Pty Limited, Sydney (AU)

(*) Notice: Subject to any disclaimer, the term of this patent is extended or adjusted under 35 U.S.C. 154(b) by 0 days.

(21) Appl. No.: 17/494,803

(22) Filed: Oct. 5, 2021

(65) Prior Publication Data

US 2023/0108267 A1   Apr. 6, 2023

(51) Int. Cl.
*A61B 5/372* (2021.01)
*G01R 33/56* (2006.01)
(Continued)

(52) U.S. Cl.
CPC ............ *A61B 5/372* (2021.01); *A61B 5/7267* (2013.01); *G01R 33/4806* (2013.01); *G01R 33/5608* (2013.01)

(58) Field of Classification Search
CPC .. A61B 5/372; A61B 5/7267; G01R 33/4806; G01R 33/5608
See application file for complete search history.

(56) References Cited

U.S. PATENT DOCUMENTS 8,742,754 B2   6/2014   Hasan
9,747,421 B2   8/2017   Krishna et al.
(Continued)

FOREIGN PATENT DOCUMENTS

WO   WO 2001/038895   5/2001
WO   WO 2014/153466   9/2014
(Continued)

OTHER PUBLICATIONS

Deligianni, F., et al., "Relating resting-state fMRI and EEG whole-brain connectomes across frequency bands," frontiers in Neuroscience. vol. 8(258), 2014. p. 1-16 (Year: 2014).*

(Continued)

*Primary Examiner* — Keith M Raymond
*Assistant Examiner* — Sean A Frith
(74) *Attorney, Agent, or Firm* — Fish & Richardson P.C.

(57) ABSTRACT

Methods, systems, and apparatus, including computer programs encoded on computer storage media, for performing EEG source localization. One of the methods includes obtaining brain data comprising: EEG data comprising respective channel data corresponding to each of a plurality of electrodes of an EEG sensor, and fMRI data comprising respective voxel data corresponding to each of a plurality of voxels; identifying, in a three-dimensional coordinate system, a respective location for each electrode; generating, using the respective identified locations of each electrode, data representing a location in the three-dimensional coordinate system of each voxel; determining, for each electrode, a region of interest in the three-dimensional coordinate system; and identifying, for each electrode, one or more corresponding parcellations in the brain of the subject, wherein each parcellation that corresponds to an electrode at least partially overlaps with the region of interest of the electrode.

16 Claims, 10 Drawing Sheets

(51) Int. Cl.
    *G01R 33/48*     (2006.01)
    *A61B 5/00*     (2006.01)

(56) References Cited

U.S. PATENT DOCUMENTS

| | | | |
|---|---|---|---|
| 11,087,877 B1 | 8/2021 | Sughrue et al. | |
| 2009/0279762 A1* | 11/2009 | Tsukimoto | G01R 33/56341 |
| | | | 382/131 |
| 2010/0004527 A1 | 1/2010 | Dale et al. | |
| 2010/0014727 A1* | 1/2010 | Hu | G06T 7/136 |
| | | | 382/128 |
| 2017/0035320 A1 | 2/2017 | Verma et al. | |
| 2017/0052241 A1 | 2/2017 | Cetingul et al. | |
| 2018/0025489 A1 | 1/2018 | Tiwari et al. | |
| 2018/0173997 A1 | 6/2018 | Shen et al. | |
| 2019/0166434 A1 | 5/2019 | Petley et al. | |
| 2020/0337625 A1* | 10/2020 | Aimone | A61B 5/7275 |
| 2021/0106830 A1* | 4/2021 | Provenza | A61B 5/4836 |
| 2021/0264623 A1* | 8/2021 | Tandon | A61B 34/10 |
| 2021/0369147 A1* | 12/2021 | Cheung | A61B 5/055 |
| 2022/0222540 A1 | 7/2022 | Sughrue et al. | |

FOREIGN PATENT DOCUMENTS

| | | |
|---|---|---|
| WO | WO 2016/083927 | 6/2016 |
| WO | WO 2018/162307 | 9/2018 |
| WO | WO 2019/100032 | 5/2019 |

OTHER PUBLICATIONS

Giacometti, P., et al., "Algorithm to find high density EEG scalp coordinates and analysis of their correspondence to structural and functional regions of the brain," Journal of Neurosci Methods. vol. 229, 2014. p. 84-96 (Year: 2014).*

Liu, X., et al., "A Convolutional Neural Network for Transcoding Simultaneously Acquired EEG-fMRI Data," 9th International IEEE EMBS Conference on Neural Engineering. 2019. p. 477-482 (Year: 2019).*

Zhai, Y., et al., "A study on the reference electrode standardization technique for a realistic head model," Computer Methods and Programs in Biomedicine. vol. 76, 2004. p. 229-238 (Year: 2004).*

Kreitz, S., et al., "A New Analysis of Resting State Connectivity and Graph Theory Reveals Distinctive Short-Term Modulations due to Whisker Stimulation in Rats," Frontiers in Neuroscience. vol. 12(334), 2018. p. 1-19 (Year: 2018).*

Coalson et al., "The impact of traditional neuroimaging methods on the spatial localization of cortical areas." Proceedings of the National Academy of Sciences, 2018, 115.27:E6356-65.

Dipy.org [online], "Introduction to Basic Tracking," retrieved on Dec. 2, 2020, retrieved from URL <https://dipy.org/documentation/1.3.0./examples_built/tracking_introduction_eudx/#example-tracking-introduction-eudx?>, 8 pages.

Giacometti et al., "Algorithm to find high density EEG scalp coordinates and analysis of their correspondence to structural and functional regions of the brain," Journal of Neuroscience Methods, vol. 229, pp. 84-96. (Year: 2014).

Huang et al., "Inverse-Transform AutoEncoder for Anomaly Detection" arXiv, 2019, 5(6):1-15.

LaPlante et al., "The Connectome Visualization Utility: Software for Visualization of Human Brain Networks," PLoS One, Dec. 2014, 9((12):1-18.

Liu et al. A convolution neural network for transcoding simultaneously acquired EEG-fMRI data. 9th International IEEE EMBS Conference on Neural Engineering, pp. 477-482. (Year: 2019).

Moreno-Donninguez, "Whole-brain Cortical Parcellation: A Hierarchical Method Based on dMRI Tractography" 2014, Ph.D. Thesis in Engineering, Max Planck Institute for Human Cognitive and Brain Sciences Leipzig, 188 pages.

Najdenovska et al., "In-vivo probabilistic atlas of human thalamic nuclei based on diffusion-weighted magnetic resonance imaging" Scientific Data, Nov. 2018, 5:180270.

Petrovic et al., "Evaluating Volumetric Brain Registration Performance Using Structural Connectivity Information", 2011, Med. Image Compuy Comput. Assist. Interv., 14(2):524-31.

pypi.org, [online] "DeepDefacer: Automatic Removal of Facial Features via Deep Learning" Jan. 13, 2019, retrieved on Dec. 2, 2020, retrieved from URL <https://pypi.org/project/deepdefacer/>, 4 pages.

Toga et al., "The role of image registration in brain mapping"; Image Vis Comput., Jan. 2001, 19(1-2): 3-24.

Urchs et al., "MIST: A multi-resolution parcellation of functional brain networks," MNI Open Research, Dec. 5, 2017, 1(3):1-30.

Xia et al., "BrainNet Viewer: A Network Visualization Tool for Human Brain Connectomics," PLoS One, Jul. 2013, 8(7):1-15.

* cited by examiner

SECOND MONTAGE 320

FIRST MONTAGE 310 fMRI IMAGE SLICES 410

EEG ELECTRODE REGIONS
OF INTEREST 600

ALIGNED MODEL
500

SOURCE LOCALIZATION OF EEG SIGNALS

CROSS-REFERENCE TO RELATED APPLICATIONS

This application is related to the U.S. patent application Ser. No. 17/145,234, filed on Jan. 8, 2021, and incorporated herein by reference in its entirety.

BACKGROUND

This specification relates to processing data related to the brain of a subject, e.g., functional magnetic resonance imaging (fMRI) data and/or electroencephalogram (EEG) data. One can derive brain functional connectivity data from fMRI and EEG data.

Brain functional connectivity data characterizes, for each of one or more pairs of locations within the brain of a subject, the degree to which brain activity in the pair of locations is correlated.

One can gather data related to the brain of the subject by obtaining and processing images of the brain of the subject, e.g., using magnetic resonance imaging (MRI), diffusion tensor imaging (DTI), or functional MRI imaging (fMRI). Diffusion tensor imaging uses magnetic resonance images to measure diffusion of water in a human brain. One can use the measured diffusion to generate tractography data, which can include images of neural tracts and corresponding white matter fibers of the subject brain.

Data related to the brain of a single subject can be highly complex and high-dimensional, and therefore difficult for a clinician to manually inspect and parse, e.g., to plan a surgery or diagnose the subject for a brain disease or mental disorder.

SUMMARY

This specification relates to source localization of EEG signals captured from the brain of a subject. In this specification, source localization is the process of identifying, for an EEG signal captured by a particular EEG electrode of an EEG sensor, a point or region of the brain of the subject that represents the source of the EEG signal.

Particular embodiments of the subject matter described in this specification can be implemented so as to realize one or more of the following advantages.

Using techniques described in this specification, a system can automatically process a set of EEG data to determine, for each electrode of the EEG sensor used to capture the EEG data, one or more regions in the brain of the patient whose brain signal is represented by the channel of the EEG data corresponding to the electrode. The system can perform source localization more consistently and with significantly higher accuracy than many existing techniques. For example, in some implementations the system can identify the single parcellation in the brain of the patient that is represented by a channel of the EEG data.

In some implementations described in this specification, a system can use a machine learning model to perform source localization. That is, the system can be fully machine-learned, without requiring human expert input. Thus, the source localization systems described in this specification can be significantly more efficient than existing techniques.

In some implementations, the system can perform source localization on EEG data corresponding to a particular montage even if the system has never before processed EEG data generated using the particular montage. In some implementations, the system can perform source localization on the EEG data even if the montage used to generate the EEG data is unknown.

Data related to the brain of a single subject can be highly complex and high-dimensional, and therefore difficult for a clinician to manually inspect and parse, e.g., to plan a surgery or diagnose the subject for a brain disease or mental disorder. For example, a connectivity matrix, e.g., a connectivity matrix of fMRI data, of the brain of a subject can be a matrix with hundreds, thousands or tens of thousands of elements.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a system that can perform source localization on EEG data.

Figure 1A:
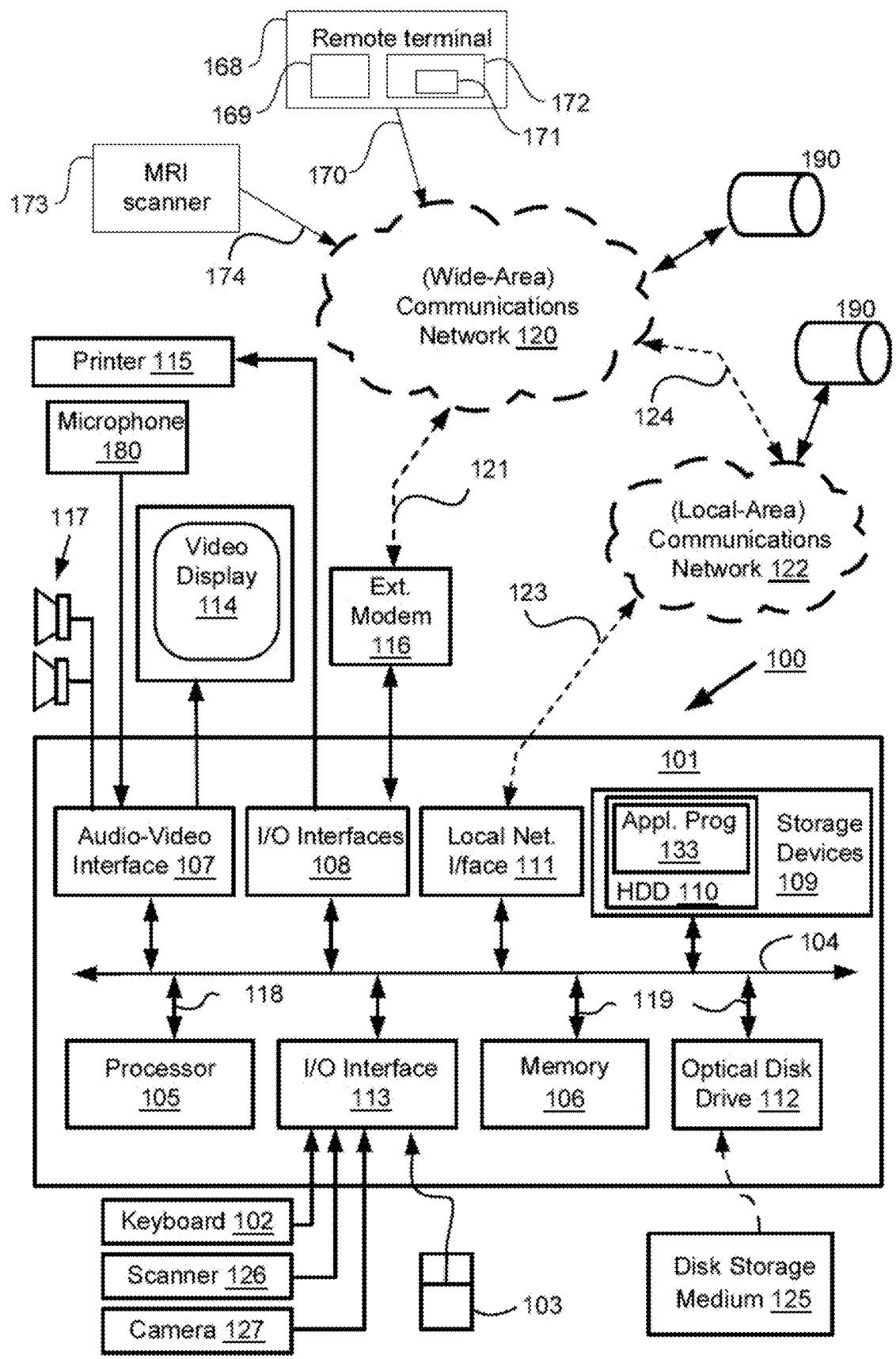
FIG. 1A and FIG. 1B are block diagrams that illustrate an example computer system for use in processing medical images.
Figure 1B:
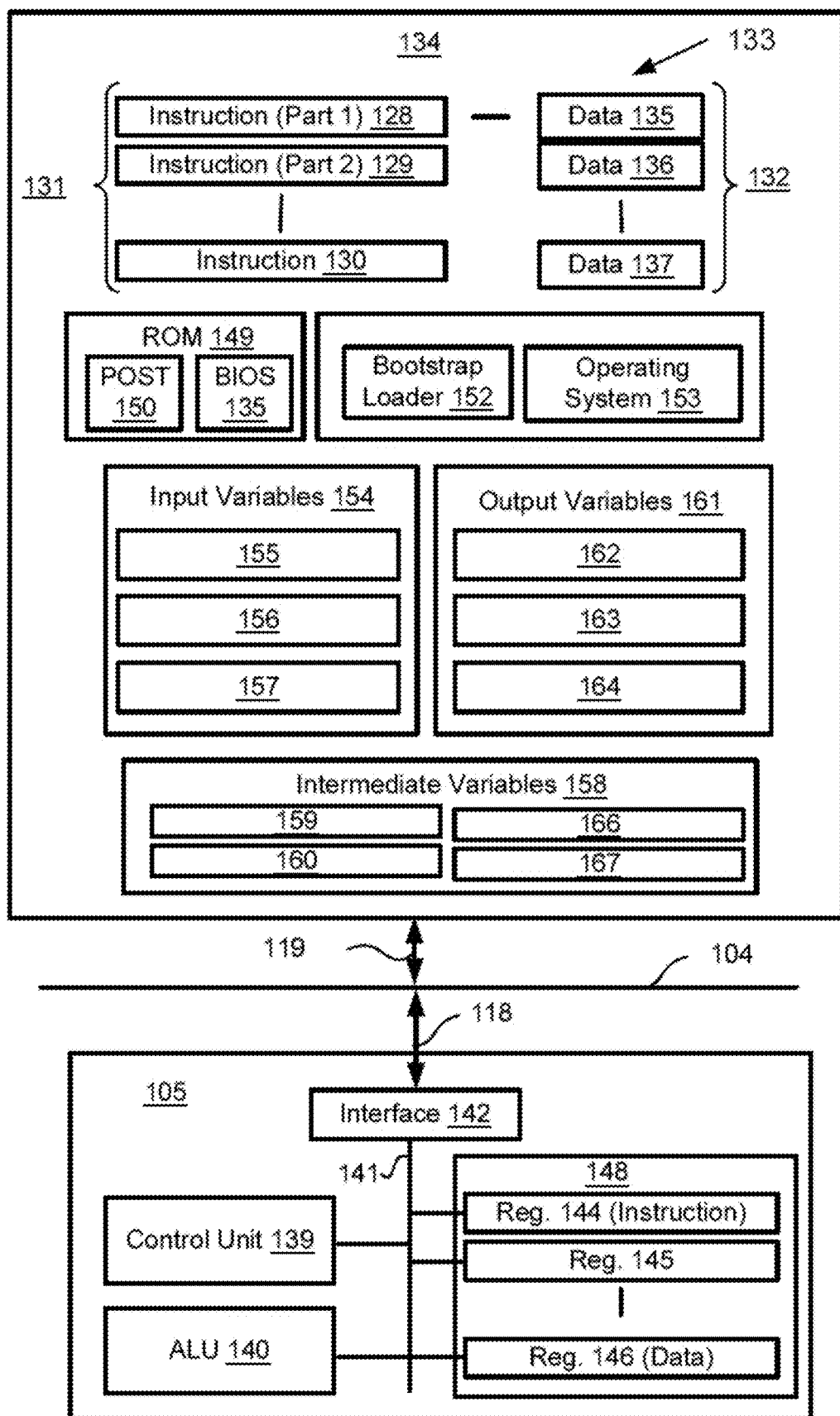

FIGS. 1A and 1B are block diagrams of a general-purpose computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. Software modules for that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a brain imaging device 173 such as an Mill or DTI scanner, across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing the brain of a subject, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include (i) a fetch operation, which fetches or reads an instruction 131 from a memory location 128, 129, 130; (ii) a decode operation in which the control unit 139 determines which instruction has been fetched; and (iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2A:
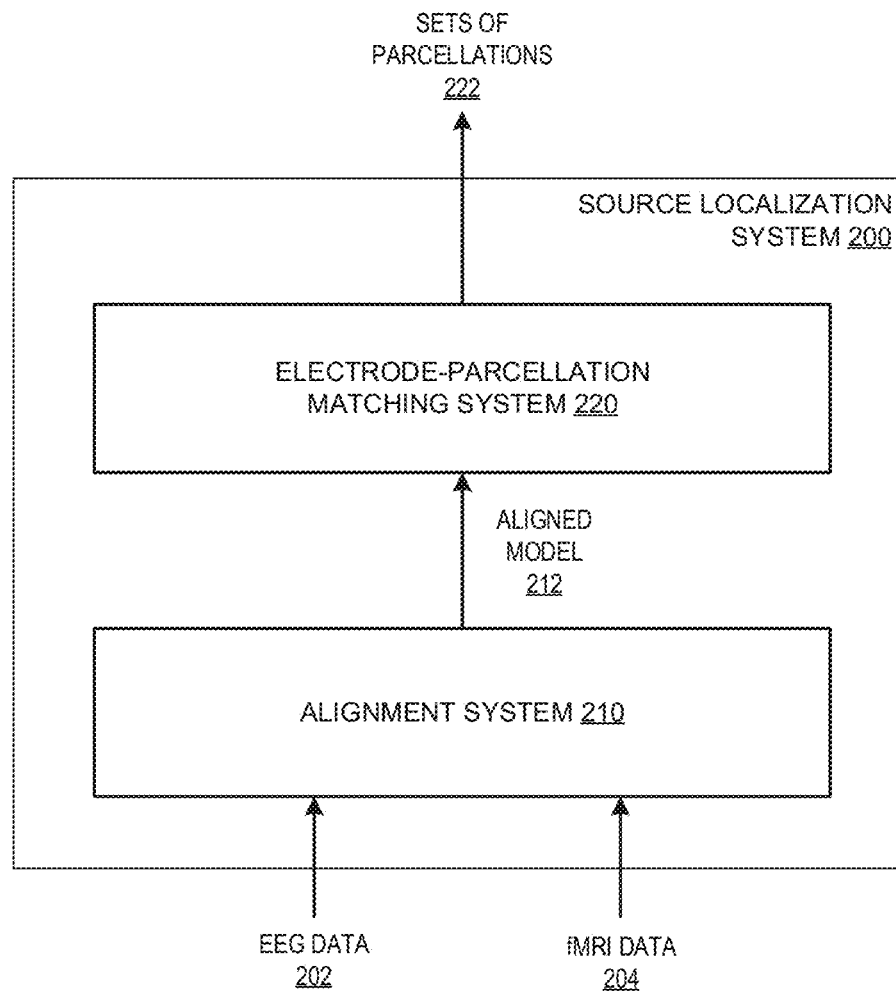
FIG. 2A, FIG. 2B, and FIG. 2C are diagrams of example source localization systems.
Figure 2B:
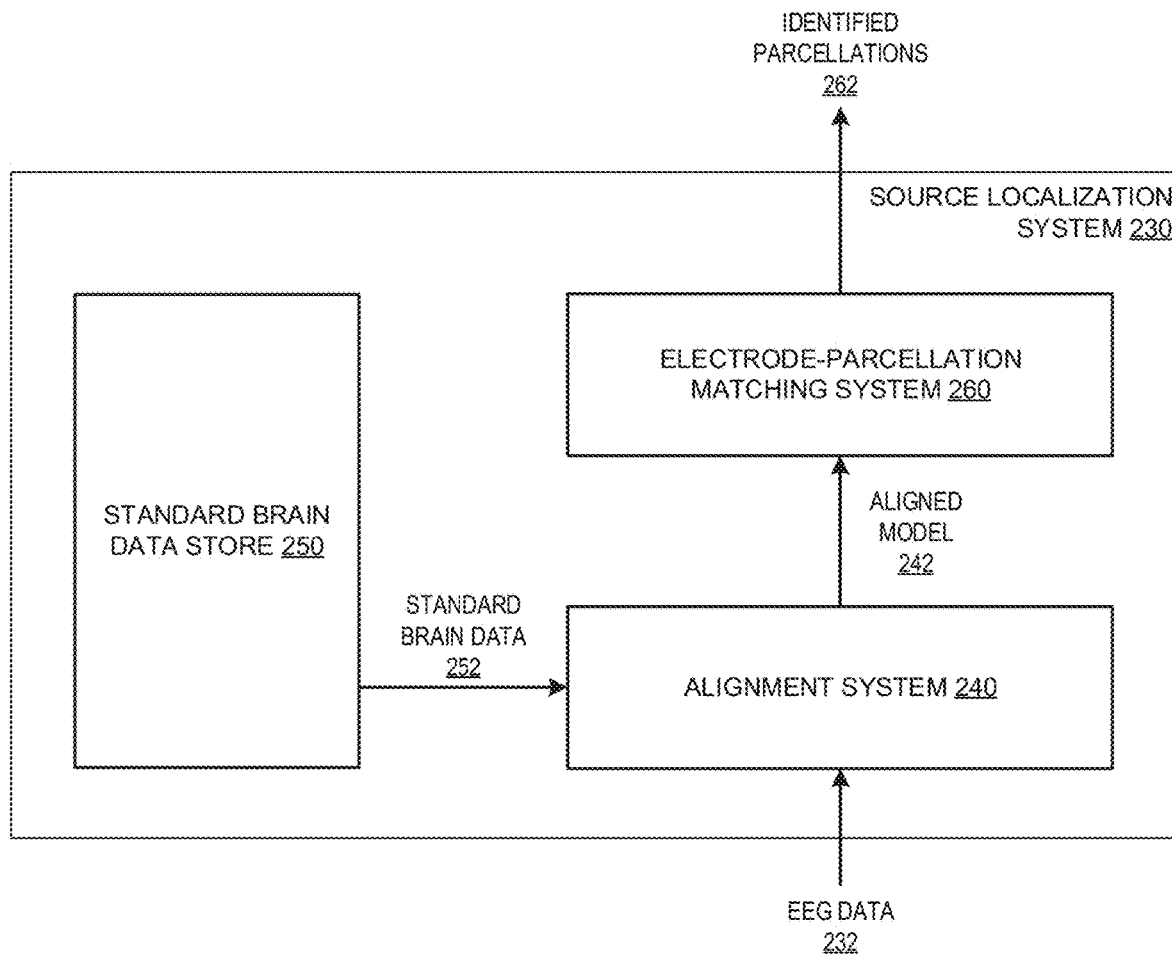
Figure 2C:
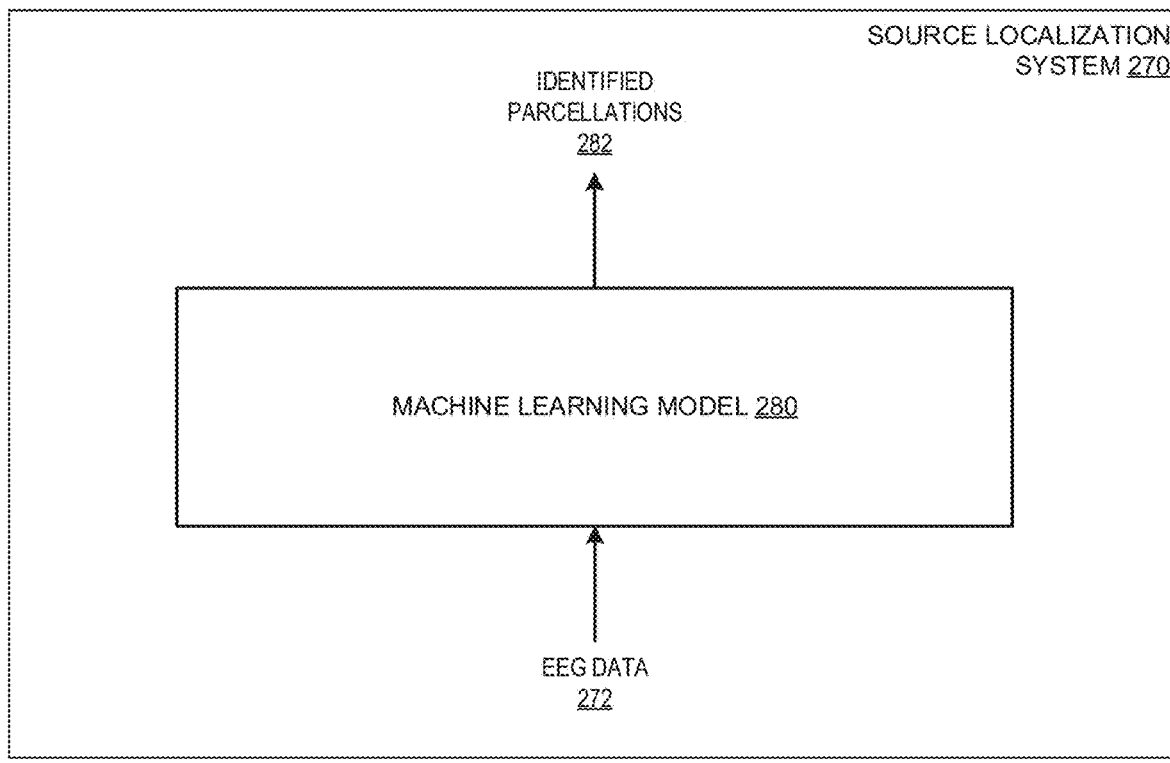

FIG. 2A, FIG. 2B, and FIG. 2C are diagrams of example source localization systems. FIG. 2A is a diagram of a source localization system 200 that is configured to process EEG data 202 and fMRI data 204 captured from the brain of a subject to perform source localization for each electrode of the EEG sensor used to capture the EEG data 202. FIG. 2B is a diagram of a source localization system 230 that is configured to process EEG data 232 without corresponding fMRI data (e.g., in situations in which fMRI data captured from the brain of the subject is unavailable) to perform source localization for each electrode of the EEG sensor used to capture the EEG data 232. FIG. 2C is a diagram of a source localization system 270 that includes a machine learning model 280 that has been configured through training to process a model input generated from EEG data 272 and to perform source localization for each electrode of the EEG sensor used to capture the EEG data 272.

Referring to FIG. 2A, the source localization system 200 includes an alignment system 210 and an electrode-parcellation matching system 220. The source localization system 200 is an example of a system implemented as computer programs on one or more computers in one or more locations in which the systems, components, and techniques described below are implemented.

The alignment system 210 is configured to process (j) a set of EEG data 202 captured from the brain of a subject and (ii) a set of fMRI data 204 captured from the brain of the same subject, and to generate data representing a three-dimensional model 212 of the brain of the subject aligned with the electrodes of the EEG sensor used to capture the EEG data 202. That is, the aligned model 212 represents the respective locations, in a common three-dimensional coordinate system, of the electrodes of the EEG sensor at the time the EEG data 202 was captured, relative to the location and orientation of the brain of the subject. The brain of the subject can be segmented into multiple regions, e.g., multiple voxels or parcellations. The aligned model 212 can include the respective location and orientation, in the common three-dimensional coordinate system, of each of the regions of the brain of the subject.

The EEG data 202 includes multiple channels each corresponding to a respective electrode of the EEG sensor used to capture the EEG data 202. Each channel of the EEG data 202 can be a time series of elements representing brain activity recorded by the corresponding electrode of the EEG sensor at respective time points. EEG electrodes generally capture brain activity from a region of the brain that is local to the location of the EEG electrode on the scalp. In this specification, the subset EEG data corresponding to a particular electrode is called the "channel data" of the electrode.

In this specification, the configuration of electrodes of an EEG sensor is called the "montage" of the EEG sensor. That is, a montage can define the location on the scalp of a subject that each electrode of an EEG sensor should be placed. In practice, each subject's head is shaped slightly differently, and so the actual location on the scalp of a given subject that an electrode of an EEG sensor is placed may differ slightly from the location defined by the montage of the EEG sensor. In some implementations, the source localization system 200 can be configured to perform source localization for EEG sensors corresponding to montages for which the source localization system 200 has never processed EEG data before. That is, the source localization system 200 can be configured to perform source localization on EEG data 202 captured according to arbitrary new montages.

Figure 3:
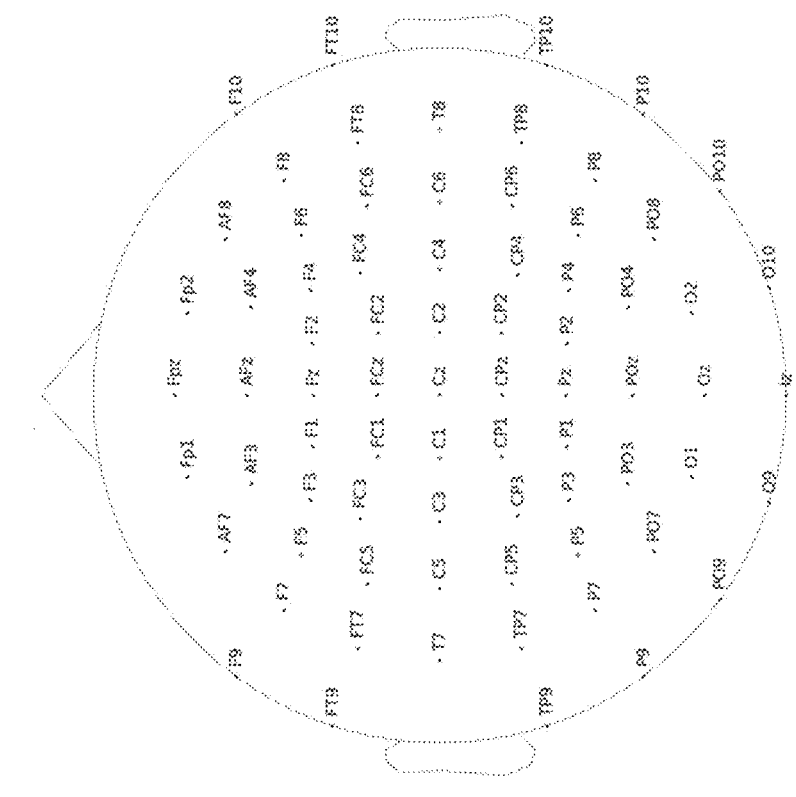
FIG. 3 illustrates example EEG montages.
Figure 3:
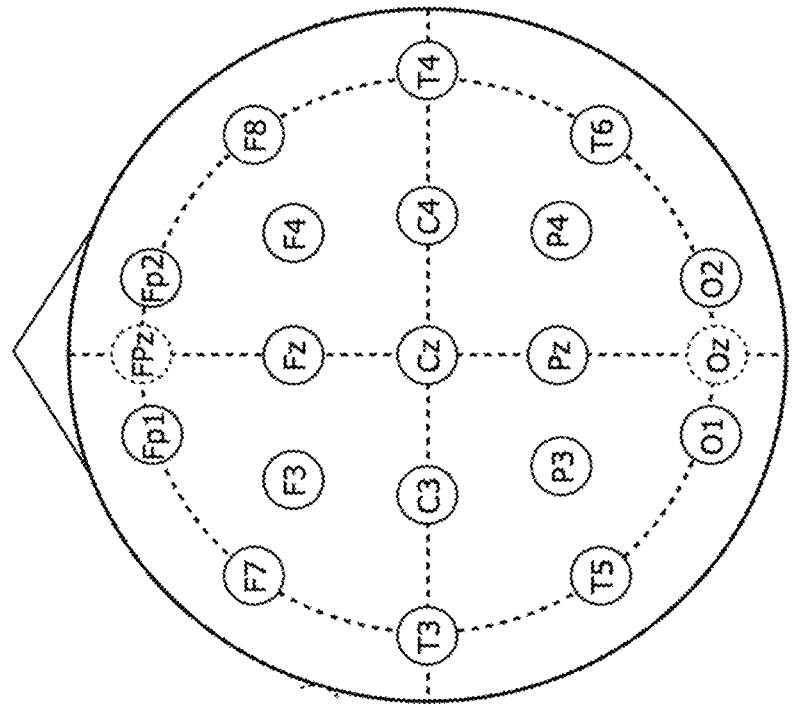

FIG. 3 illustrates example EEG montages 310 and 320. The montages 310 and 320 characterize the placement of electrodes of respective EEG sensors on the scalp of subjects. In particular, the first montage 310 corresponds to an EEG sensor that has 21 electrodes, while the second montage 320 corresponds to an EEG sensor that has 74 electrodes.

Because each subject's head is shaped slightly differently, the electrodes of the EEG montages 310 and 320 can capture the brain activity of slightly different regions of the brain of each subject.

Referring back to FIG. 2A, the fMRI data 204 can includes respective data corresponding to each of multiple regions in the brain of the subject, e.g., each voxel in a grid of voxels representing the brain of the subject. In this specification, the subset of fMRI data corresponding to a particular voxel is called the "voxel data" of the voxel. Although this specification generally refers to voxels in the brain of a subject, generally fMRI data can include data corresponding to any appropriate type of region of the brain of the subject.

In some implementations, the EEG data 202 and the fMRI data 204 were captured from the brain of the subject at the same time. In some other implementations, the EEG data 202 and the fMRI data 204 were captured from the brain of the subject at different times.

To generate the aligned model 212, the alignment system 210 can identify a point in the fMRI data 204 that is closest to the top of the head of the subject. For example, if the fMRI data 204 includes respective data corresponding to each voxel in a grid of voxels, the alignment system 210 can identify one voxel or a set of contiguous voxels that are closest to the top of the head of the subject. In this specification, the top of the head of a subject is the point on the head of the subject that is highest along a vertical axis that extends approximately along the neck and spine of the subject.

For example, the fMRI data 204 can include a sequence of image slices each corresponding to a respective position along a vertical axis of the brain of the subject, e.g., image slices at a regular interval along the vertical axis of the brain of the subject. Each image slice can include a subset of the voxels from the voxel grid that are aligned in the vertical axis at the position corresponding to the image slice.

Figure 4:
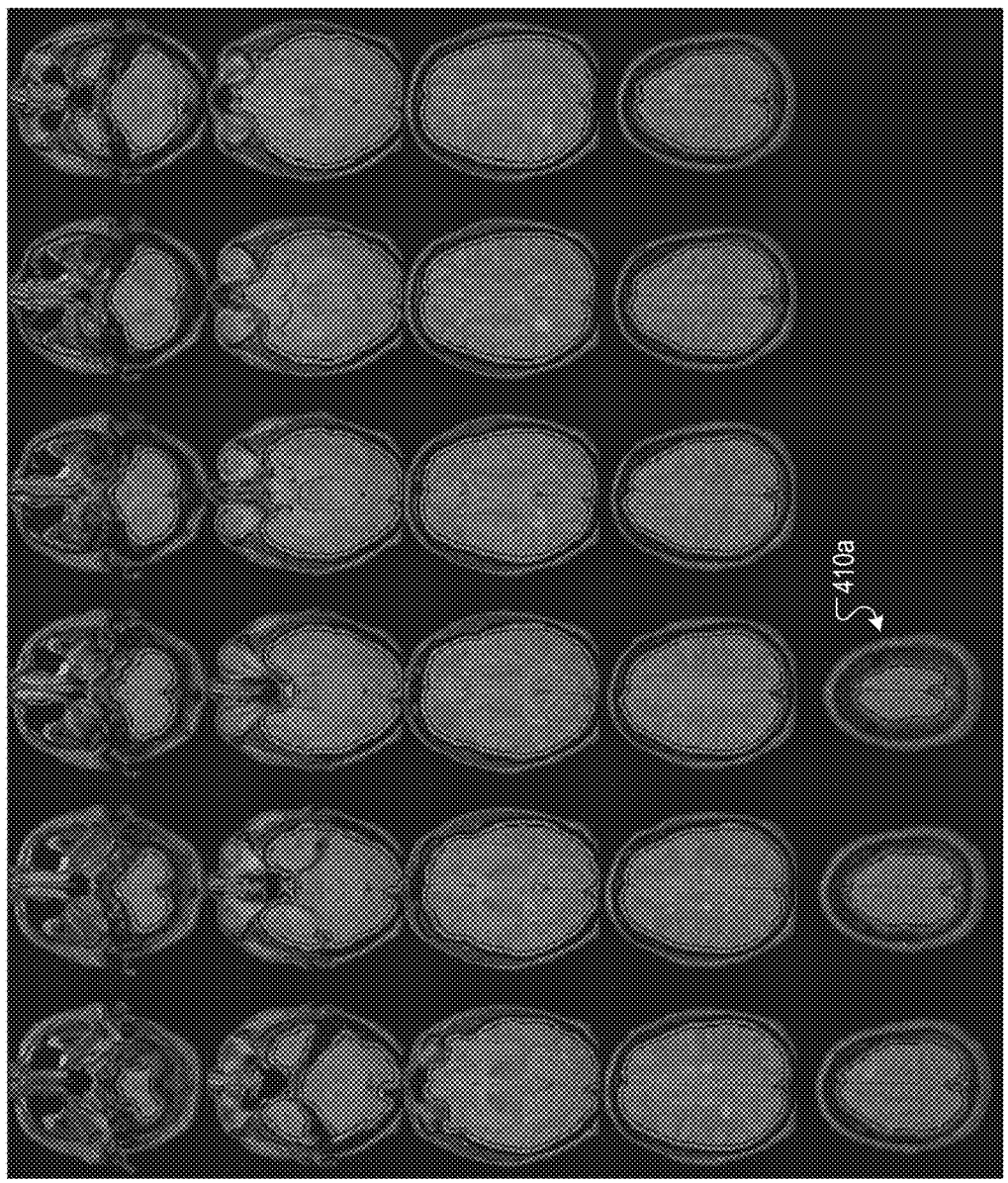
FIG. 4 illustrates example fMRI image slices.

FIG. 4 illustrates example fMRI image slices 410. The fMRI image slices 410 have been generated from fMRI data captured from the brain of a subject. Each fMRI image slice 410 corresponds to a respective position along a vertical axis of the brain of the subject, i.e., an axis that extends approximately from the neck of the subject to the top of the head of the subject. Each fMRI image slice 410

Referring back to FIG. 2A, the alignment system 210 can identify the topmost image slice in the sequence, i.e., the image slice that is highest along the vertical axis of the brain of the subject.

In some implementations, one or more of the image slices in the sequence do not include any voxels that represent the brain of the subject. For example, the sequence of image slices can include one or more image slices corresponding to positions along the vertical axis that are higher or lower than any point on the brain of the subject. In these implementations, the alignment system 210 can identify the topmost images slice that represents a portion of the brain of the subject, i.e., the image slice that (i) is highest along the vertical axis and (ii) that includes at least one voxel representing the brain of the subject. For convenience, in this specification voxels that represent the brain of the subject are called "brain voxels" and voxels that do not represent the brain of the subject are called "non-brain voxels."

For example, the alignment system 210 can binarize each image slice so that each voxel of the image slice is identifies as either (i) a brain voxel (e.g., as identified by a value of '1' in the binarized image slice), or (ii) a non-brain voxel (e.g., as identified by a value of '0' in the binarized image slice). The alignment system 210 can then identify the image slice that is the highest, along the vertical axis, of all the image slices that include at least one brain voxel (e.g., at least one voxel with a value of '1' in the binarized image slice).

In the example depicted in FIG. 4, the alignment system 210 can determine the image slice 410*a* to be the topmost image slice of the fMRI image slices 410.

After identifying the topmost image slice, the alignment system 210 can identify one or more brain voxels in the topmost image slice that are closest to the top of the head of the subject. For convenience, in this specification the brain voxels that are determined to be closest to the top of the head of the subject are called "top voxels." For example, the alignment system 210 can binarize the topmost image slice as described above, so that each voxel in the topmost image slice is identified as either a brain voxel or a non-brain voxel. As a particular example, the alignment system 210 can determine the center of mass of the brain voxels of the topmost image slice (e.g., the center of mass of the voxels that have a value of '1' in the binarized topmost image slice). That is, the set of brain voxels in the topmost image slice can collectively be modeled as a two-dimensional shape, and the alignment system 210 can determine the top voxel to be the brain voxel that includes the center of mass of the two-dimensional shape. The alignment system 210 can use any appropriate technique to determine the center of mass of the two-dimensional shape. As another particular example, the alignment system 210 can determine a bounding box of the brain voxels of the topmost image slice, and determine the top voxel to be the brain voxel that includes the center point of the bounding box.

After determining the one or more top voxels in the fMRI data 204, the alignment system 210 can generate the aligned model 212 in which the one or more top voxels are aligned, in a common three-dimensional coordinate system of the aligned model 212, with a reference electrode of the EEG sensor that captured the EEG data 202. The reference electrode of the EEG sensor can be an electrode that is typically placed at or near the top of the head of the subject. For example, the reference electrode can be the "center-zero" electrode, or "CZ" electrode, in the International 10-20 System of electrode placement. In particular, the alignment system 210 can assign each brain voxel in the fMRI data 204 a respective location, e.g., a respective (x, y, z) location, in the common three-dimensional coordinate system of the aligned model 212. Similarly, the alignment system 210 can assign the reference electrode a location in the common three-dimensional coordinate system of the aligned model 212, where the location of the reference electrode is determined based on the respective locations of the one or more top voxels.

For example, if there is a single top voxel, the alignment system 210 can assign, to the reference electrode, the same location in the common three-dimensional coordinate system as the top voxel. As another example, if there is a single top voxel, the alignment system 210 can assign, to the reference electrode, a location that is a predetermined distance above the location of the top voxel in the common three-dimensional coordinate system. That is, if the location of the top voxel is $(x_1, y_1, z_1)$ and the z-axis is the vertical axis of the coordinate system (i.e., the axis that approximately aligns with the neck and spine of the subject), then the aligned model can assign, to the reference electrode, the location $(x_1, y_1, z_1+\varepsilon)$, where $\varepsilon$ is the predetermined distance. Adding a predetermined distance along the vertical axis to the location of the reference electrode can account for the skull of the patient, since the EEG electrodes are not applied directly to the brain of the subject but rather to the scalp of the subject.

As another example, if there is a set of multiple top voxels, the alignment system 210 can assign, to the reference electrode, the average location of the multiple top voxels in the common three-dimensional coordinate system. As another example, if there is a set of multiple top voxels, the alignment system 210 can assign, to the reference electrode, a location that is a predetermined distance above the average location of the multiple top voxels in the common three-dimensional coordinate system.

After assigning a location to the reference electrode of the EEG sensor, the alignment system 210 can use the location of the reference electrode to determine a respective location, in the common three-dimensional coordinate system, for each other electrode of the EEG sensor.

The alignment system 210 can first determine a respective initial location for each electrode of the EEG sensor, in a coordinate system corresponding to the EEG sensor. In some implementations, the initial locations accurately identify the relative positioning of the electrodes at the time the EEG data 202 was captured from the brain of the patient. For example, the EEG data 202 can include metadata that identifies, in a coordinate system defined by the EEG sensor, a respective location for each electrode at the time the EEG data 202 was captured from the brain of the subject. That is, the EEG data 202 can include metadata defining the relative positions of the EEG electrodes when applied specifically to the scalp of the subject—thus, generally, this metadata is different for each subject. In some other implementations, the initial locations represent the montage of the EEG sensor; that is the initial locations corresponding to a montage can be the same for all subjects regardless of differing head shapes.

The alignment system 210 can use the initial locations of the electrodes in the coordinate system corresponding to the EEG sensor to determine respective locations of the electrodes in the common coordinate system of the aligned model 212.

In some implementations, the alignment system 210 first projects the initial location of each non-reference electrode into the common coordinate system of the aligned model 212, then scales the projected locations to fit the non-reference electrodes to the scalp of the subject.

For example, using (i) the initial location of the reference electrode in the coordinate system corresponding to the EEG sensor and (ii) the location of the reference electrode in the common coordinate system of the aligned model 212, the alignment system 210 can determine a mapping between the two coordinate systems, i.e., a transformation that can be applied to initial locations in the coordinate system corresponding to the EEG sensor to project the locations into the common coordinate system of the aligned model 212. For example, the transformation can be defined by the difference between (i) the initial location of the reference electrode in the coordinate system corresponding to the EEG sensor and (ii) the location of the reference electrode in the common coordinate system of the aligned model 212.

Generally, the relative scales of (i) the coordinate system defined by the EEG sensor and (ii) the common coordinate system of the aligned model 212 are different. That is, the distance between two real-world points (e.g., the real-world size of the brain of the subject) is different when expressed in the respective coordinate systems. This can cause scaling issues when projecting the initial locations of the EEG electrodes into the common coordinate system. For example, the scale of the coordinate system defined by the EEG sensor can be larger than the scale of the common coordinate system, such that the projected locations of the non-reference electrodes are too distant from each other (i.e., some or all of the projected locations of the non-reference electrodes are too far away from the brain voxels in the common coordinate system, even though the reference electrode is properly aligned with the top voxels). Alternatively, the scale of the coordinate system defined by the EEG sensor can be smaller than the scale of the common coordinate system, such that the projected locations of the non-reference electrodes are too close to each other (i.e., some or all of the projected locations of the non-reference electrodes are too close to, or even within, the brain voxels in the common coordinate system, even though the reference electrode is properly aligned with the top voxels).

Thus, after projecting the location of each non-reference electrode into the common coordinate system of the aligned model 212, the alignment system 210 can apply a scaling factor to each projected location to align the projected location with the brain voxels in the aligned model 212. The scaling procedure is centered at the reference electrode, such that the location of the reference electrode in the common coordinate system does not change when the scaling factor is applied. For example, the alignment system 210 can minimize the average distance between the non-reference electrodes and the closest brain voxels in the aligned model 212. That is, for a given scaling factor and for each non-reference electrode, the alignment system 210 can apply the scaling factor to the non-reference electrode and determine the distance between (i) the scaled location of the non-reference electrode and (ii) the brain voxel that is closest to the non-reference electrode in the common coordinate system of the aligned model 212. The alignment system 210 can then adjust the scaling factor to minimize the average of the distances for the non-reference electrodes. As a particular example, the alignment system 210 can perform gradient descent on the scaling factor to minimize the average distance.

In some other implementations, the alignment system 210 first scales the initial locations of the electrodes, in the coordinate system corresponding to the EEG sensor, to match the scale of the common coordinate system of the aligned model 212, then projects the scaled locations into the common coordinate system of the aligned model 212.

For example, the alignment system 210 can generate a three-dimensional volume, in the coordinate system corresponding to the EEG sensor, that is within the points representing the initial locations of the electrodes and that represents the brain or scalp of the subject. As a particular example, the alignment system 210 can determine the convex hull of the respective initial locations of the electrodes of the EEG sensor; the convex hull represents a volume in the coordinate system corresponding to the EEG sensor that is the smallest possible volume in the coordinate system that encloses each of the points corresponding to the EEG electrodes. Because the initial locations of the electrodes correspond to the real-world locations at which the electrodes were placed on the scalp of the subject, the convex hull approximately models the scalp of the subject. As another particular example, the alignment system 210 can determine the convex hull of the initial locations of the electrodes in the coordinate system corresponding to the EEG sensor, then apply a small scaling factor (e.g., a predetermined scaling factor) to the convex hull to account for the skull of the subject (i.e., so that the convex hull approximately models the brain of the subject).

The alignment system 210 can match the determined volume (e.g., the convex hull) in the coordinate space corresponding to the EEG sensor with the volume represented by the brain voxels in the common coordinate system of the aligned model 212. For example, the alignment system 210 can project the two volumes into the same coordinate system (e.g., either the coordinate system corresponding to the EEG sensor or the common coordinate system of the aligned model 212), aligning the reference electrode with the top voxels as described above. The alignment system 210 can then determine a scaling factor to apply to the determined volume (centered at the reference electrode, as described above) that minimizes the disjunctive union of (i) the determined volume and (ii) the volume represented by the brain voxels. The disjunctive union of two volumes is the set of all points that are inside one of the two volumes but outside the other of the two volumes. Thus, minimizing the disjunctive union between (i) the determined volume and (ii) the volume represented by the brain voxels causes the two volumes to be approximately aligned, and to have approximately the same size. As a particular example, the alignment system 210 can perform gradient descent on the scaling factor to minimize the disjunctive union.

After matching the determined volume (e.g., the convex hull) in the coordinate space corresponding to the EEG sensor with the volume represented by the brain voxels in the common coordinate system of the aligned model 212, the alignment system 210 can use the matching to project the initial locations of the non-reference electrodes into the common coordinate space of the aligned model 212. For example, the alignment system 210 can apply the same scaling factor that was applied to the convex hull in order to minimize the disjunctive union, as described above, to the respective initial location of each non-reference electrode in the coordinate system corresponding to the EEG sensor. The alignment system 210 can then project the scaled location of each non-reference electrode into the common coordinate system of the aligned model 212 using (i) the scaled location of the reference electrode in the coordinate system corresponding to the EEG sensor and (ii) the location of the reference electrode in the common coordinate system of the aligned model 212, as described above.

In some implementations, after aligning each electrode of the EEG sensor with the brain voxels in the aligned model 212, the alignment system 210 applies a transformation to the respective location of each electrode of the EEG sensor to account for the skull of the subject (e.g., if the alignment system 210 did not perform one or more of the techniques to account for the skull of the subject described above). For example, the alignment system 210 can translate the location, in the common coordinate system, of each electrode by a predetermined distance away from the brain voxel that is closest to the electrode. As a particular example, given the set of locations in the common coordinate system of the electrode, the alignment system 210 can execute a dilation function that translates each location outward from a single central reference location, e.g., the center of the brain of the subject or the mean location of the electrodes.

Figure 5:
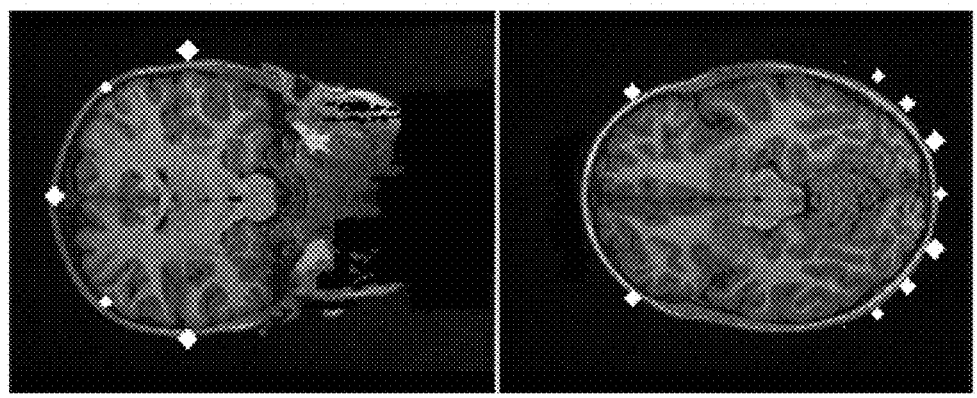
FIG. 5 illustrates an example aligned model generated from EEG data and fMRI data.

FIG. 5 illustrates an example aligned model 500 generated from EEG data and fMRI data captured from the brain of the same subject. For example, an alignment system, e.g., the alignment system 210 described above with reference to FIG. 2A, can generate the aligned model 500 from the EEG data and fMRI data.

The aligned model 500 includes respective locations, in a common coordinate space, of (i) a set of EEG electrodes of the EEG sensor that captured the EEG data and (ii) a set of voxels of the fMRI data that represent respective regions of the brain of the subject. In particular, the aligned model 500 represents the relative locations of the EEG electrodes and voxels at the time the EEG data was captured from the brain of the subject.

The top image of FIG. 5 is an image slice of the aligned model 500 at a particular position along a horizontal axis of the model 500, where the horizontal axis extends approximately from the front of the head of the subject (i.e., the face of the subject) to the back of the head of the subject. The bottom image of FIG. 5 is an image slice of the aligned model 500 at a particular position along a vertical axis of the model 500, where the vertical axis extends approximately from the neck of the subject to the top of the head of the subject.

The locations of EEG electrodes are represented by white diamonds in the images of the aligned model 500 illustrated in FIG. 5, while the voxels of the brain of the subject are represented by respective grayscale points.

Referring back to FIG. 2A, the alignment system 210 can provide the aligned model 212, which includes a respective location for each EEG electrode of the EEG sensor that captured the EEG data 202 and each brain voxel of the fMRI data 204, to the electrode-parcellation matching system 220. The electrode-parcellation matching system 220 is configured to use the aligned model 212 to determine, for each electrode of the EEG sensor, a set 222 of one or more corresponding parcellations in the brain of the subject that may have been the source of the EEG signal captured by the electrode.

The parcellations in the brain of the subject can be defined by a brain atlas. In this specification, a brain atlas is data that defines one or more parcellations of a brain of a subject, e.g., by defining in a common three-dimensional coordinate system the coordinates of the parcellation, the three-dimensional boundary of the parcellation, and/or the volume of the parcellation.

Although this specification generally refers to identifying parcellations in the brain of the subject to be the source of an EEG signal, generally a source localization system (e.g., the source localization system 200 depicted in FIG. 2A, the source localization system 230 depicted in FIG. 2B, and the source localization system 270 depicted in FIG. 2C) can identify any appropriate type of region of the brain of the subject as the source of an EEG signal. For example, a source localization system can identify one or more voxels in the brain of the subject as the source of an EEG signal.

In some implementations, for each electrode of the EEG sensor, the electrode-parcellation matching system 220 generates a set 222 that includes the one or more parcellations whose respective locations (as defined by the brain atlas) are closest to the location of the electrode in the aligned model 212.

In some other implementations, for each electrode of the EEG sensor, the electrode-parcellation matching system 220 generates a region of interest around the location of the electrode in the aligned model 212, e.g., a region of interest defined by a volume in the common coordinate system of the aligned model 212. For example, for each electrode, the electrode-parcellation matching system 220 can generate a region of interest that is a sphere of a predetermined size whose center is the location of the electrode in the aligned model 212. As a particular example, the size of the sphere can be selected such that it approximately corresponds to the maximum distance within the brain of the subject that the electrode is able to measure. As another particular example, the size of the sphere can be selected using the distance between the electrodes on the scalp of the subject; e.g., the radius of the sphere can be determined to be half the mean distance between adjacent electrodes. The electrode-parcellation matching system 220 can then use the generated regions of interest to generate the set 222 of one or more parcellations corresponding to the electrode.

Figure 6:
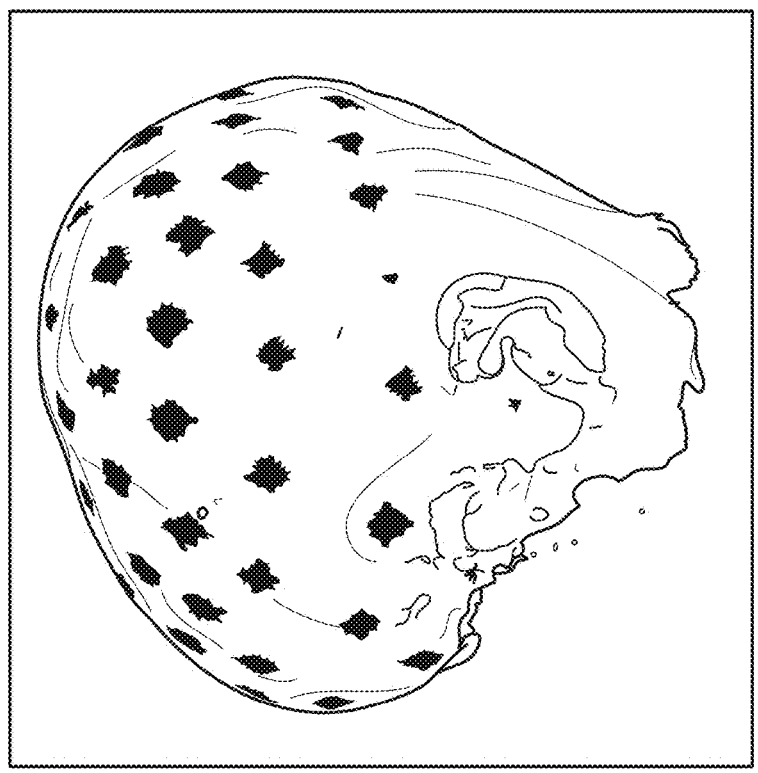
FIG. 6 illustrates example EEG electrode regions of interest.

FIG. 6 illustrates example regions of interest 600 of respective electrodes of an EEG sensor on the head of a subject. The head of the subject is represented by the white, three-dimensional model depicted in FIG. 6. For each electrode of the EEG sensor, the intersection between (i) the region of interest 600 of the electrode and (ii) the scalp of the subject is represented by a darker color on the head of the subject.

Referring back to FIG. 2A, for each electrode of the EEG sensor, after generating the respective region of interest for the electrode, the electrode-parcellation matching system 220 can determine which parcellations in the brain of the subject intersect with the region of interest of the electrode. For each parcellation in the brain of the subject, the electrode-parcellation matching system 220 can identify one or more brain voxels in the aligned model 212 that are within the boundaries of the parcellation defined by the brain atlas. The electrode-parcellation matching system 220 can then determine, for each parcellation, whether one or more brain voxels of the parcellation are within the region of interest of the electrode.

In some implementations, the electrode-parcellation matching system 220 includes, in the set 222 of parcellations corresponding to each EEG electrode, each parcellation that intersects with the region of interest of the electrode (i.e., each parcellation that includes at least one brain voxel within the region of interest). In some other implementations, the electrode-parcellation matching system 220 includes, in the set 222 of parcellations corresponding to each EEG electrode, each parcellation that includes at least a threshold number N of brain voxels in the region of interest of the electrode, N>1.

In some implementations, the electrode-parcellation matching system 220 includes at most M parcellations in the set 222 of parcellations corresponding to each electrode, M≥1. For example, if more than M parcellations intersect with the region of interest of the electrode, then the electrode-parcellation matching system 220 can select the M parcellations that have the greatest number of brain voxels in the region of interest. As another example, if more than M parcellations intersect with the region of interest of the electrode, then the electrode-parcellation matching system 220 can select the M parcellations that have the greatest proportion of their brain voxels (of all brain voxels corresponding to the parcellation) in the region of interest.

After generating the respective set 222 of parcellations corresponding to each electrode of the EEG sensor, the electrode-parcellation matching system 220 can provide the generated sets 222 to an external system for storage or further processing, e.g., one or more of: a correlation system, a graphical user interface, a machine learning system, or a training system.

The correlation system can determine, for each pair of electrodes of the EEG sensor, the correlation between the EEG signals of the pair of electrodes. The correlation system can then determine the correlation between the brain activity of the parcellations represented by the electrodes (i.e., the one or more parcellations in the respective sets 222 of parcellations corresponding to the pair of electrodes) to be a function of the correlation between the pair of electrodes, e.g., equal to the correlation between the pair of electrodes. The correlations between the brain activity of respective pairs of parcellations can be represented, e.g., using a connectivity matrix.

The graphical user interface can display, to a user, data characterizing the respective set 222 of parcellations corresponding to each electrode.

The machine learning system can include one or more machine learning models that are configured to process the EEG data 202, according to the respective sets 222 of parcellations, and generate a model output that is clinically relevant for a user. For example, a machine learning model can process the EEG data 202 to generate a prediction for whether the subject has a particular brain disease, e.g., autism, depression, or schizophrenia.

The training system can be configured to train one or more machine learning models using the sets 222 of parcellations, e.g., the machine learning model 280 described below with reference to FIG. 2C. For example, the training system can train a machine learning model to process EEG data and to generate a prediction, for each electrode of the EEG sensor used to capture the EEG data, of the source of the EEG signal captured by the electrode. The EEG data 202 and the determined sets 222 of parcellations can be used as training data by the training system. In particular, the EEG data 202 can be a training input to the machine learning model, and the sets 222 can represent the ground-truth output corresponding to the training input, i.e., the model output that the machine learning model should generate in response to processing the EEG data 202. That is, the training system can train the machine learning model to automatically identify the set 222 of parcellations corresponding to each set of channel data in the EEG data 202, without requiring the EEG data 202 (and/or the fMRI data 204) to be processed by the source localization system 200 or the source localization system 230 described below with reference to FIG. 2B. As a particular example, the source localization system 200 can provide the generated sets 222 to the training system 700 described below with reference to FIG. 7.

In some implementations, the one or more parcellations in the each set 222 corresponding to a respective electrode are "candidate" parcellations, i.e., are parcellations that the source localization system 200 has determined to be candidates as the source of the EEG signal captured by the electrode. In these implementations, the source localization system 200 (or an external system that has obtained the sets 222 from the source localization system) is further configured to select, for each set 222 of candidate parcellations, one or more of the candidate parcellations from the set 222 to be the "final" parcellations that are predicted to be the source of the EEG signal captured by the corresponding electrode.

For example, the source localization system 200 (or an external system) can be configured to compare, for each candidate parcellation corresponding to each electrode, (i) the channel data of the EEG data 202 corresponding to the electrode and (ii) the subset of the fMRI data 204 corresponding to the candidate parcellation in order to determine whether the candidate parcellation should be selected as a final parcellation for the electrode. For example, for each candidate parcellation corresponding to an electrode, the source localization system 200 can obtain the voxel data of the fMRI data 204 corresponding to each voxel in the candidate parcellation, and compare the obtained sets of voxel data with the channel data corresponding to the electrode. For instance, the source localization system 200 can determine the mean of the voxel data across all voxels in the candidate parcellation, and compare the mean voxel data with the channel data corresponding to the electrode. In this specification, the subset of fMRI data corresponding to a parcellation is called the "parcellation fMRI data" of the parcellation.

As a particular example, for each candidate parcellation corresponding to each electrode, the source localization system 200 (or an external system) can compute a correlation between (i) the channel data of the EEG data 202 corresponding to the electrode and (ii) the parcellation fMRI data of the fMRI data 204 corresponding to the candidate parcellation. That is, if both the channel data and the parcellation fMRI data are time series representing the same amount of time, e.g., having the same number of time steps, then the source localization system 200 can determine the correlation between the two time series over the time period defined by the respective time series (even in implementations in which the EEG data 202 and the fMRI data 204 were not captured at the same time). The source localization system 200 can then select the one or more final parcellations from the set of candidate parcellations of an electrode to be the candidate parcellations with the highest correlation with the channel data of the electrode. The source localization system 200 can use any appropriate technique to determine the correlation, e.g., Pearson correlation, Kendall rank correlation, Spearman correlation, or the Point-Biserial correlation.

As another particular example, for each candidate parcellation corresponding to each electrode, the source localization system 200 (or an external system) can process one or more of (i) the channel data of the EEG data 202 corresponding to the electrode or (ii) the parcellation fMRI data of the fMRI data 204 corresponding to the candidate parcellation using a trained machine learning model.

In some implementations, the machine learning model can be configured through training to process, for a particular candidate parcellation and electrode, both the channel data of the electrode and the parcellation fMRI data of the candidate parcellation to generate a model output representing the similarity between the channel data and parcellation fMRI data, e.g., a model output that includes a value between 0 and 1 that represents the similarity. The source localization system 200 can then select the one or more final parcellations, from the set of candidate parcellations of the electrode, to be the candidate parcellations whose respective model outputs indicate the highest similarity with the channel data of the electrode. For example, the source localization system 200 can select the candidate parcellations whose respective model outputs satisfy a predetermined threshold. As another example, the source localization system 200 can select the N candidate parcellations whose respective model outputs indicate the highest similarity, N≥1. As another example, the source localization system 200 can select up to N candidate parcellations whose respective model outputs satisfy a predetermined threshold, N≥1. That is, if more than N candidate parcellations have a model output that satisfies the predetermined threshold, then the source localization system 200 can select the N candidate parcellations whose respective model outputs indicate the highest similarity.

In some other implementations, the machine learning model can be configured through training to process, for a particular candidate parcellation, only the channel data of the electrode to generate a model output identifying the one or more final parcellations. For example, the model output can include a respective score, for each parcellation in a set of parcellations (e.g., for each parcellation in the brain of the subject or for each parcellation proximal to the surface of the brain of the subject), representing a likelihood that the electrode measured the parcellation when capturing the channel data. The source localization system 200 can use the model output to select the one or more final parcellations corresponding to the electrode, e.g., by selecting the one or more parcellations that (i) are in the set of candidate parcellations for the electrode and (ii) have the highest corresponding likelihood in the model output.

Example machine learning models are described in more detail below with reference to FIG. 2C.

Referring to FIG. 2B, the source localization system 230 is configured to obtain EEG data 232 and to process the EEG data 232 to perform source localization for each electrode of the EEG sensor used to capture the EEG data 232. That is, the source localization system 230 does not obtain fMRI data captured from the brain of the same subject as the EEG data 232. For example, such fMRI data may be unavailable.

The source localization system 230 includes an alignment system 240, a standard brain data store 250, and an electrode-parcellation matching system 260. The source localization system 230 is an example of a system implemented as computer programs on one or more computers in one or more locations in which the systems, components, and techniques described below are implemented.

The alignment system 230 is configured to process the EEG data 232 and to generate data representing a three-dimensional model 242 of the electrodes of the EEG sensor used to capture the EEG data 202, aligned with a model of a "standard" brain. In this specification, a standard brain is data representing a typical brain of a population of subjects. That is, the standard brain does not represent the brain of any specific subject, but rather represents an expectation of the result of randomly sampling the brain of a subject from the population of subjects. The population of subjects can be defined in any appropriate way. For example, the population of subjects can include every human subject. As another example, the population of subjects can include every human subject that satisfies one or more criteria, e.g., criteria defined by the demographics of the subject (e.g., sex, race, and so on) or a diagnostic status of the subject (for instance, all human subjects that have dementia).

In other words, because the alignment system 240 does not have access to fMRI data characterizing the actual brain of the subject from whose brain the EEG data 232 was captured, the alignment system 240 generates an aligned model 242 that aligns the electrodes with the standard brain and that therefore is expected to represent a reasonable approximation of the alignment between the electrodes and the actual brain of the subject at the time the EEG data 232 was captured.

In particular, the alignment system 240 can obtain data 252 representing a three-dimensional model of the standard brain from the standard brain data store 250, which is configured to maintain the data 252. The standard brain data 252 can include data identifying, for each of multiple regions in the standard brain (e.g., each voxel in a grid of voxels), the location of the region in a three-dimensional coordinate system of the standard brain data 252.

As described above, the EEG data 232 includes multiple channels each corresponding to a respective electrode of the EEG sensor used to capture the EEG data 232. In some implementations, the source localization system 230 can be configured to perform source localization for EEG sensors corresponding to montages for which the source localization system 230 has never processed EEG data before.

To generate the aligned model 242, the alignment system 240 can identify a point in the standard brain data 252 that is closest to the top of the standard brain. For example, if the data 252 includes respective data corresponding to each voxel in a grid of voxels, the alignment system 240 can identify one voxel or a set of contiguous voxels that are closest to the top of the standard brain. As a particular example, the standard brain data 252 can include data identifying the one or more voxels that are to be considered the "top voxels" of the standard brain. Although the following description refers to the top voxels of the standard brain, it is to be understood that generally the top of the brain can be represented by any appropriate type of region of the brain After determining the one or more top voxels in the standard brain data 252, the alignment system 240 can generate the aligned model 242 in which the one or more top voxels are aligned, in the common three-dimensional coordinate system of the aligned model 242, with a reference electrode of the EEG sensor that captured the EEG data 232. In particular, the alignment system 240 can assign each voxel in the standard brain data 252 a respective location, e.g., a respective (x, y, z) location, in the common three-dimensional coordinate system of the aligned model 242. Similarly, the alignment system 210 can assign the reference electrode a location in the common three-dimensional coordinate system of the aligned model 242, where the location of the reference electrode is determined based on the respective locations of the one or more top voxels. The alignment system 240 can align the one or more top voxels with the reference electrode using any appropriate technique, e.g., one or more of the techniques described above with reference to FIG. 2A.

After assigning a location to the reference electrode of the EEG sensor, the alignment system 240 can use the location of the reference electrode to determine a respective location, in the common three-dimensional coordinate system, for each other electrode of the EEG sensor. For example, as described above, the EEG data 232 can include metadata that identifies, in a coordinate system defined by the EEG sensor, a respective location for each electrode at the time the EEG data 232 was captured from the brain of the subject. The alignment system 240 can use any appropriate technique to project the respective locations of the non-reference electrodes from the coordinate system defined by the EEG sensor to the common coordinate system of the aligned model 242, e.g., one or more of the techniques described above with reference to FIG. 2A.

The alignment system 240 can provide the aligned model 242, which includes a respective location for each EEG electrode of the EEG sensor that captured the EEG data 232 and each voxel of the standard brain data 252, to the electrode-parcellation matching system 260. The electrode-parcellation matching system 260 is configured to use the aligned model 242 to determine, for each electrode of the EEG sensor, a set 262 of one or more corresponding parcellations in the brain of the subject that may have been the source of the EEG signal captured by the electrode. The electrode-parcellation matching system 260 can use any appropriate technique to generate the set 262 of parcellations for each electrode, e.g., one or more of the techniques described above with reference to FIG. 2A.

After generating the respective set 262 of parcellations corresponding to each electrode of the EEG sensor, the electrode-parcellation matching system 260 can provide the generated sets 262 to an external system for storage or further processing, e.g., one or more of: a correlation system, a graphical user interface, a machine learning system, or training system, as described above with reference to FIG. 2A.

In some implementations, the one or more parcellations in the each set 262 corresponding to a respective electrode are "candidate" parcellations. In these implementations, the source localization system 230 (or an external system that has obtained the sets 262 from the source localization system) is further configured to select, for each set 262 of candidate parcellations, one or more of the candidate parcellations from the set 262 to be the "final" parcellations that are predicted to be the source of the EEG signal captured by the corresponding electrode. For example, as described above with reference to FIG. 2A, for each candidate parcellation corresponding to each electrode, the source localization system 230 can process one or more of (i) the channel data of the EEG data 202 corresponding to the electrode or (ii) the parcellation fMRI data of the fMRI data 204 corresponding to the candidate parcellation using a trained machine learning model. Example machine learning models are described in more detail below with reference to FIG. 2C.

Referring to FIG. 2C, the source localization system 270 is configured to obtain EEG data 272 and to process the EEG data 272 to perform source localization for each electrode of the EEG sensor used to capture the EEG data 272. The source localization system 270 is an example of a system implemented as computer programs on one or more computers in one or more locations in which the systems, components, and techniques described below are implemented.

The source localization system 270 includes a machine learning model 280. The machine learning model 280 is configured to process the EEG data 272 and to identify, for each electrode of the EEG sensor, a set 282 of one or more parcellations whose brain signal may have been measured by the electrode when capturing the channel of the EEG data 272.

For example, the machine learning model 280 can be configured to process the channel data of the EEG data 272 corresponding to an electrode, and to generate a model output that includes a respective score for each parcellation in a set of parcellations. The score for a particular parcellation can identify the likelihood that the channel data represents the brain activity of the particular parcellation; for instance, each score can be a value between 0 and 1, where a higher value represents a higher likelihood that the electrode measured brain activity in the parcellation. The machine learning model 280 can then select one or more parcellations with the highest scores to include in the set 282 corresponding to the electrode.

The set of parcellations identified in the model output can be any appropriate set. For example, the set can include every parcellation in the brain of the subject. As another example, the set can include only those parcellations that are proximal to the surface of the brain, e.g., only cortical parcellations or only parcellations that are within a threshold distance (e.g., less than 2 cm, less than 3 cm or less than 4 cm) of the surface of the brain (or less than 2 cm, less than 3 cm or less than 4 cm from an electrode in question).

As a particular example, the machine learning model 280 can include a recurrent neural network, e.g., a long short-term memory (LSTM) neural network or a gated recurrent unit (GRU) neural network, that is configured to process each element of the channel data recurrently. That is, the channel data of the EEG data 272 corresponding to a particular electrode can include the time series of raw voltage values measured by the particular electrode, and the recurrent neural network can process the time series of values recurrently at respective processing time steps to generate a network output identifying the set 282 of parcellations for the particular electrode.

In particular, at each processing time step, the recurrent neural network can process (i) the next element in the time series and (ii) a hidden state of the recurrent neural network in order to update the hidden state of the recurrent neural network. In one or more of the processing time steps (in some implementations, at each processing time step), the recurrent neural network can also generate the model output corresponding to the current element in the time series data. The recurrent neural network can then process the one or more network outputs generated at respective processing time steps to generate the model output for the particular parcellation. For example, the recurrent neural network can process the final network output (i.e., the network output generated at the final processing time step) using one or more feedforward neural network layers and/or a softmax layer to generate the model output. As another example, the recurrent neural network can combine the one or more network outputs (e.g., by determining the average of the network outputs), and process the combined network output (e.g., using one or more feedforward neural network layers and/or a softmax layer) to generate the model output.

Example techniques for training the machine learning model 280 are described below with reference to FIG. 7.

In some implementations, as described above, the source localization system 280 can be configured to perform source localization for EEG sensors corresponding to montages for which the source localization system 230 has never processed EEG data before.

In some implementations, the source localization system 280 can be configured to perform source localization for EEG sensor for which no montage information is available. That is, the source localization system 280 does not need to have access to information characterizing how the EEG electrodes were placed on the head of the subject at the time the EEG data 272 was captured. Rather, the machine learning model 280 can determine the appropriate source for each channel based on patterns within the EEG data 272 itself.

Figure 7:
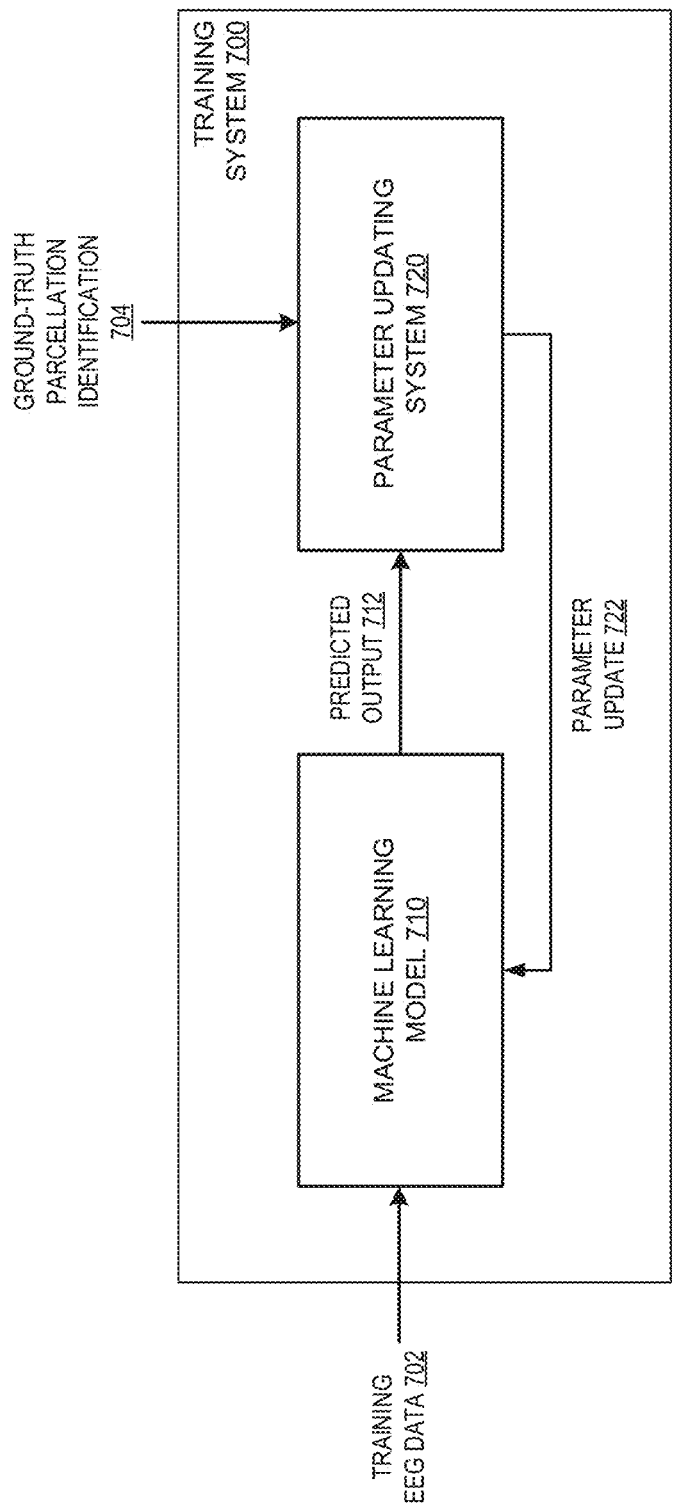
FIG. 7 is a diagram of an example training system for training a machine learning model to perform EEG source localization.

FIG. 7 is a diagram of an example training system 700 for training a machine learning model 710 to perform EEG source localization. The training system 700 is an example of a system implemented as computer programs on one or more computers in one or more locations in which the systems, components, and techniques described below are implemented.

The training system 700 includes the machine learning model 710 and a parameter updating system 720. The training system 700 is configured train the machine learning model 710 to process EEG data to generate model outputs that identify, for each electrode of the EEG sensor used to capture the EEG data, one or more parcellations that may be the source of the EEG signal captured by the electrode.

In particular, the training system 700 is configured to obtain training examples that each include (i) training EEG data 702 and (ii) a ground-truth identification 704, for each channel of the training EEG data 702, of the parcellation corresponding to the channel. That is, the ground-truth identification 704 represents what the machine learning model 710 should generate in response to processing the training EEG data 702. For example, the ground-truth identifications 704 can be generated by a source localization system, e.g., the source localization systems 200 and 230 described above.

For each set of training EEG data 702, the training system 700 can process the training EEG data 702 using the machine learning model 710 to generate a predicted output 712 that identifies the one or more parcellations that are predicted to correspond to each respective electrode of the EEG sensor.

After generating the predicted output 712, the training system 700 can provide the predicted output 712 to the parameter updating system 720, which is configured to determine a parameter update 722 to the parameters of the machine learning model 710 according to an error between (i) the predicted output 712 and (ii) the ground-truth identification 704. The training system 700 can use any appropriate classification loss function, e.g., categorical cross entropy loss or KL divergence. In some implementations, the parameter updating system 700 updates the parameters of the machine learning model 710 using gradient descent and backpropagation.

In some implementations, after the training system 700 has completed training of the machine learning model 710 (i.e., after the training system 700 has generated final parameter values for the machine learning model 710), the machine learning model 710 can be deployed on an inference system that is configured to perform source localization on new sets of EEG data. In some implementations, the training system 700 can train the machine learning model 710 to perform source localization on EEG data for which no montage information is available, i.e., access to information characterizing how the EEG electrodes were placed on the head of the subject at the time the EEG data was captured.

In some such implementations, at inference time, the inference system can receive EEG data that has been captured using an EEG sensor that has a montage that was not seen during training. Even if the machine learning model 710 has never received EEG data corresponding to the particular montage before, the machine learning model 710 can generate predictions of the source of each channel of the EEG data.

Figure 8:
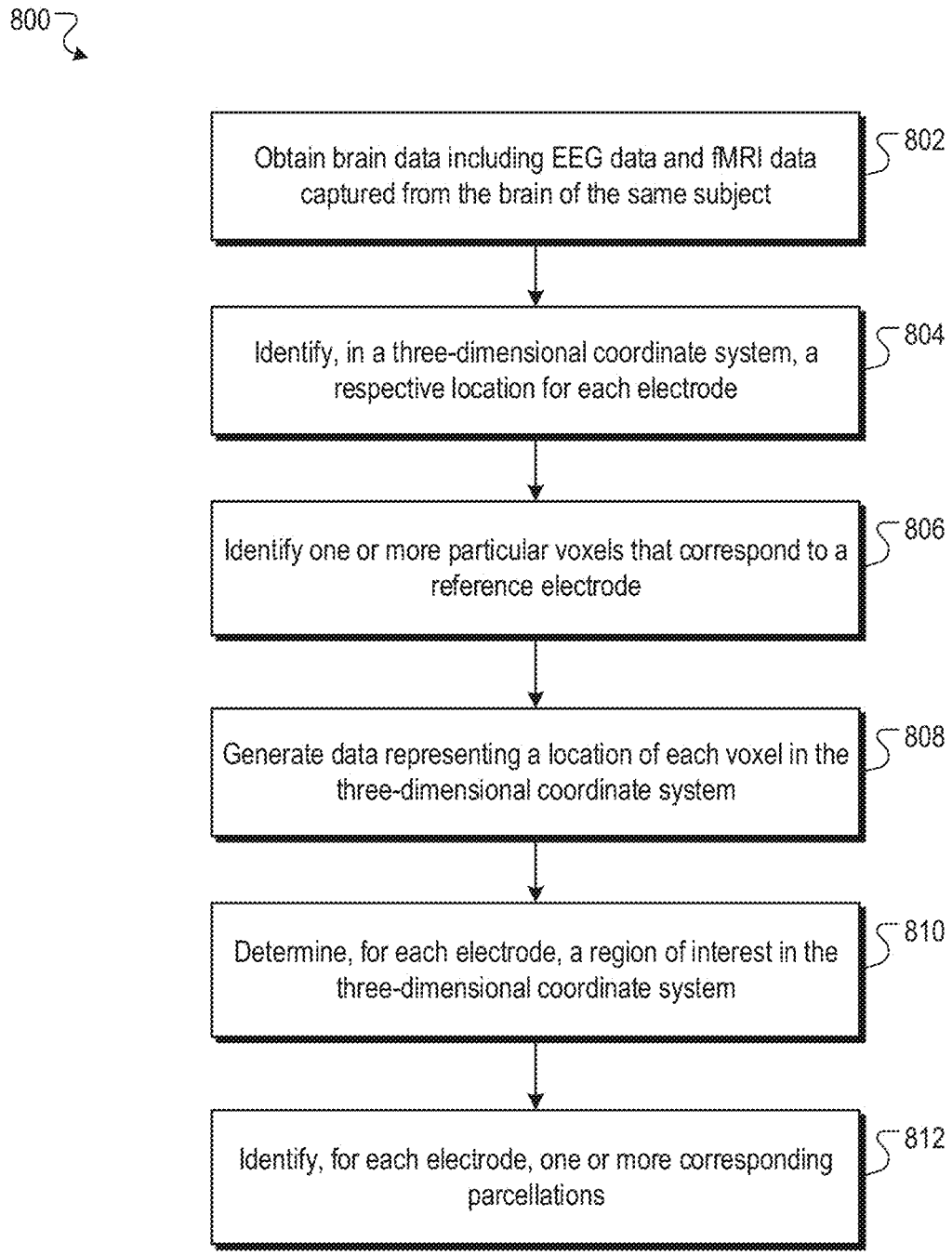
FIG. 8 is a flowchart of an example process for performing EEG source localization.

FIG. 8 is a flowchart of an example process for performing EEG source localization. The process 800 can be implemented by one or more computer programs installed on one or more computers and programmed in accordance with this specification. For example, the process 800 can be performed by the computer server module depicted in FIG. 1A. For convenience, the process 800 will be described as being performed by a system of one or more computers.

The system obtains brain data that includes EEG data and fMRI data captured from the brain of the same subject (step 802). The EEG data can include respective channel data corresponding to each of multiple electrodes of an EEG sensor. The fMRI data can include respective voxel data corresponding to each of multiple voxels, where the voxel data of each voxel represents a respective region of a respective parcellation in the brain of the subject.

The system identifies, in a three-dimensional coordinate system, a respective location for each electrode of the multiple electrodes (step 804).

The system identifies one or more particular voxels of the multiple voxels that correspond to a reference electrode of the multiple electrodes of the EEG sensor (step 806).

The system generates data representing a location in the three-dimensional coordinate system of each voxel of the multiple voxels. (step 808). For example, the system can align, in the three-dimensional coordinate system, the one or more particular voxels and the reference electrode of the EEG sensor.

The system determines, for each electrode of the multiple electrodes, a region of interest in the three-dimensional coordinate system (step 810).

The system identifies, for each electrode of the multiple electrodes, one or more corresponding parcellations in the brain of the subject, where each parcellation that corresponds to an electrode at least partially overlaps with the region of interest of the electrode (step 812).

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g, a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method comprising:
obtaining brain data comprising:
EEG data captured from a brain of a subject, the EEG data comprising respective channel data corresponding to each of a plurality of electrodes of an EEG sensor; and
fMRI data captured from the brain of the subject, the fMRI data comprising respective voxel data corresponding to each of a plurality of voxels, wherein the voxel data of each voxel represents a respective region of a respective parcellation in the brain of the subject;
identifying, in a three-dimensional coordinate system, a respective location for each electrode of the plurality of electrodes;
generating, using the respective identified locations of each electrode of the plurality of electrodes, data representing a location in the three-dimensional coordinate system of each voxel of the plurality of voxels;
determining, for each electrode of the plurality of electrodes, a region of interest in the three-dimensional coordinate system; and
identifying, for each electrode of the plurality of electrodes, one or more corresponding parcellations in the brain of the subject, wherein each parcellation that corresponds to an electrode at least partially overlaps with the region of interest of the electrode.

Embodiment 2 is the method of embodiment 1, wherein identifying, for each electrode of the plurality of electrodes, one or more corresponding parcellations comprises:
identifying, from the plurality of voxels of the fMRI data, a plurality of first voxels whose location in the three-dimensional coordinate system overlaps with the region of interest of the electrode;
determining, for each first voxel, the parcellation that the first voxel represents; and
identifying at least one parcellation that is represented by one or more respective first voxels overlapping with the electrode.

Embodiment 3 is the method of any one of embodiments 1 or 2, wherein identifying, for each electrode of the plurality of electrodes, one or more corresponding parcellations comprises:

identifying a plurality of candidate parcellations;

for each candidate parcellation, processing (i) the channel data of the EEG data corresponding to the electrode and (ii) the voxel data of the fMRI data corresponding to the candidate parcellation to determine a similarity between the channel data of the EEG data and the voxel data of the fMRI data; and selecting at least one of the candidate parcellations according to their respective similarities.

Embodiment 4 is the method of any one of embodiments 1-3, further comprising:

generating (i) a training input comprising the channel data of the EEG data corresponding to the electrode and (ii) a ground-truth output identifying one or more parcellations whose brain activity was captured by the channel data of the EEG data corresponding to the electrode; and training a machine learning model using the training input and the ground-truth output, wherein the machine learning model is configured to process first channel data captured by an electrode and to generate a prediction of a parcellation represented by the first channel data.

Embodiment 5 is the method of embodiment 4, wherein the machine learning model comprises a recurrent neural network that processes an EEG time series captured by an electrode and generates a network output comprising, for each of a plurality of first parcellations, a value representing a likelihood that the EEG time series represents the first parcellation.

Embodiment 6 is the method of any one of embodiments 1-5, wherein generating data representing a location in the three-dimensional coordinate system of each voxel of the plurality of voxels comprises:

identifying one or more particular voxels of the plurality of voxels that correspond to a reference electrode of the plurality of electrodes of the EEG sensor; and aligning, in the three-dimensional coordinate system, the one or more particular voxels and the reference electrode of the EEG sensor.

Embodiment 7 is the method of embodiment 6, wherein identifying one or more particular voxel that correspond to the reference electrode comprises:

determining, from the fMRI data, a plurality of image slices, wherein each image slice represents the brain of the subject at a different elevation along a vertical axis of the three-dimensional coordinate system;

identifying a particular image slice that represents a topmost region of the brain of the subject;

determining the particular voxel to be a voxel represented by the particular image slice.

Embodiment 8 is the method of embodiment 7, wherein identifying the particular image slice that represents the topmost region of the brain of the subject comprises:

processing each image slice to generate a respective binarized image slice, wherein each pixel of each binarized image slice has a value that identifies whether the pixel represents the brain of the subject or not;

determining the particular image slice to be the preceding image slice, along the vertical axis, before a first image slice that does not include any pixels representing the brain of the subject.

Embodiment 9 is the method of any one of embodiments 7 or 8, wherein determining the one or more particular voxels comprises:

determining a center of mass of the pixels of the particular image slice that represent the brain of the subject; and determining the one or more particular voxels to be a set of one or more voxels that includes the determined center of mass.

Embodiment 10 is the method of any one of embodiments 1-9, wherein the region of interest of each electrode is a sphere with a same radius.

Embodiment 11 is a method comprising:

obtaining EEG data captured from a brain of a subject, the EEG data comprising respective channel data corresponding to each of a plurality of electrodes of an EEG sensor;

obtaining voxel data characterizing a plurality of voxels, wherein the voxel data of each voxel represents a respective region of a respective parcellation in a typical brain;

identifying, in a three-dimensional coordinate system, a respective location for each electrode of the plurality of electrodes;

generating, using the respective identified locations of each electrode of the plurality of electrodes, data representing a location in the three-dimensional coordinate system of each voxel of the plurality of voxels;

determining, for each electrode of the plurality of electrodes, a region of interest in the three-dimensional coordinate system; and identifying, for each electrode of the plurality of electrodes, one or more corresponding parcellations in the brain of the subject, wherein each parcellation that corresponds to an electrode at least partially overlaps with the region of interest of the electrode.

Embodiment 12 is the method of embodiment 11, wherein identifying, for each electrode of the plurality of electrodes, one or more corresponding parcellations comprises:

identifying, from the plurality of voxels, a plurality of first voxels whose location in the three-dimensional coordinate system overlaps with the region of interest of the electrode;

determining, for each first voxel, the parcellation that the first voxel represents; and identifying at least one parcellation that is represented by one or more respective first voxels overlapping with the electrode.

Embodiment 13 is the method of any one of embodiments 11 or 12, further comprising:

generating (i) a training input comprising the channel data of the EEG data corresponding to the electrode and (ii) a ground-truth output identifying one or more parcellations whose brain activity was captured by the channel data of the EEG data corresponding to the electrode; and training a machine learning model using the training input and the ground-truth output, wherein the machine learning model is configured to process first channel data captured by an electrode and to generate a prediction of a parcellation represented by the first channel data.

Embodiment 14 is the method of embodiment 13, wherein the machine learning model comprises a recurrent neural network that processes an EEG time series captured by an electrode and generates a network output comprising, for each of a plurality of first parcellations, a value representing a likelihood that the EEG time series represents the first parcellation.

Embodiment 15 is the method of any one of embodiments 11-14, wherein generating data representing a location in the three-dimensional coordinate system of each voxel of the plurality of voxels comprises:

identifying one or more particular voxels of the plurality of voxels that correspond to a reference electrode of the plurality of electrodes of the EEG sensor; and aligning, in the three-dimensional coordinate system, the one or more particular voxels and the reference electrode of the EEG sensor.

Embodiment 16 is the method of embodiment 15, wherein identifying one or more particular voxel that correspond to the reference electrode comprises:

determining, from the voxel data, a plurality of image slices, wherein each image slice represents the brain of the subject at a different elevation along a vertical axis of the three-dimensional coordinate system;

identifying a particular image slice that represents a topmost region of the brain of the subject;

determining the particular voxel to be a voxel represented by the particular image slice.

Embodiment 17 is the method of embodiment 16, wherein identifying the particular image slice that represents the topmost region of the brain of the subject comprises:

processing each image slice to generate a respective binarized image slice, wherein each pixel of each binarized image slice has a value that identifies whether the pixel represents the brain of the subject or not;

determining the particular image slice to be the preceding image slice, along the vertical axis, before a first image slice that does not include any pixels representing the brain of the subject.

Embodiment 18 is the method of any one of embodiments 16 or 17, wherein determining the one or more particular voxels comprises:

determining a center of mass of the pixels of the particular image slice that represent the brain of the subject; and determining the one or more particular voxels to be a set of one or more voxels that includes the determined center of mass.

Embodiment 19 is the method of any one of embodiments 11-18, wherein the region of interest of each electrode is a sphere with a same radius.

Embodiment 20 is a method comprising:

obtaining EEG data captured from a brain of a subject, the EEG data comprising respective channel data corresponding to each of a plurality of electrodes of an EEG sensor; and for each electrode of the plurality of electrodes of the EEG sensor:

generating a model input from the channel data corresponding to the electrode; and processing the model input using a machine learning model to generate a model output that predicts an identify of a particular parcellation, from a plurality of parcellations in the brain of the subject, whose brain activity is represented by the channel data corresponding to the electrode, wherein the machine learning model has been trained using a training data set comprising a plurality of training examples corresponding to respective second subjects, wherein each training example comprises (i) a training input comprising EEG channel data captured from a brain of the respective second subject and (ii) a ground-truth output identifying a parcellation whose brain activity was captured by the EEG channel data.

Embodiment 21 is the method of embodiment 20, wherein, for each of one or more particular training examples of the plurality of training examples, the ground-truth output of the particular training example has been generated using the method of any one of claims 1-19.

Embodiment 22 is the method of any one of embodiments 20 or 21, wherein, for each electrode of the plurality of electrodes of the EEG sensor, the model input comprises the channel data corresponding to the electrode.

Embodiment 23 is a system comprising one or more computers and one or more storage devices storing instructions that are operable, when executed by the one or more computers, to cause the one or more computers to perform the method of any one of embodiments 1-22.

Embodiment 24 is a computer storage medium encoded with a computer program, the program comprising instructions that are operable, when executed by data processing apparatus, to cause the data processing apparatus to perform the method of any one of embodiments 1-22.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

What is claimed is:

1. A method comprising:

obtaining brain data comprising:

EEG data captured from a brain of a subject, the EEG data comprising respective channel data corresponding to each of a plurality of electrodes of an EEG sensor, and fMRI data captured from the brain of the subject, the fMRI data comprising respective voxel data corresponding to each of a plurality of voxels, wherein the voxel data of each voxel represents a respective region of a respective parcellation in the brain of the subject;

identifying, in a three-dimensional coordinate system, a respective location for each electrode of the plurality of electrodes;

generating, using the respective identified locations of each electrode of the plurality of electrodes, data representing a location, in the three-dimensional coordinate system, of each voxel of the plurality of voxels, the generating comprising:
identifying one or more particular voxels of the plurality of voxels that correspond to a reference electrode of the plurality of electrodes of the EEG sensor, the identifying comprising:
determining, from the fMRI data, a plurality of image slices, wherein each image slice represents the brain of the subject at a different elevation along a vertical axis of the three-dimensional coordinate system;
identifying a particular image slice that represents a topmost region of the brain of the subject by processing at least some of the plurality of image slices to generate respective binarized image slices, wherein each pixel of each binarized image slice has a value that identifies whether the pixel represents the brain of the subject or not; and determining the particular image slice to be a preceding image slice, along the vertical axis, before a first image slice that does not include any pixels representing the brain of the subject;
determining a center of mass of a set of pixels of the particular image slice, where the set of pixels have been determined to represent the brain of the subject; and
determining the one or more particular voxels to include a voxel that includes the determined center of mass; and
aligning, in the three-dimensional coordinate system, the one or more particular voxels and the reference electrode of the EEG sensor;
determining, for each electrode of the plurality of electrodes, a region of interest in the three-dimensional coordinate system, wherein the region of interest of each electrode is a sphere having a predetermined size; and
identifying, for each electrode of the plurality of electrodes, one or more corresponding parcellations in the brain of the subject, wherein each parcellation that corresponds to an electrode at least partially overlaps with the region of interest of the electrode.

2. The method of claim 1, wherein identifying, for each electrode of the plurality of electrodes, one or more corresponding parcellations comprises:
identifying, from the plurality of voxels of the fMRI data, a plurality of first voxels whose location in the three-dimensional coordinate system overlaps with the region of interest of the electrode;
determining, for each first voxel, the parcellation that the first voxel represents; and
identifying at least one parcellation that is represented by one or more respective first voxels overlapping with the electrode.

3. The method of claim 1, wherein identifying, for each electrode of the plurality of electrodes, one or more corresponding parcellations comprises:
identifying a plurality of candidate parcellations;
for each candidate parcellation, processing (i) the channel data of the EEG data corresponding to the electrode and (ii) the voxel data of the fMRI data corresponding to the candidate parcellation to determine a similarity between the channel data of the EEG data and the voxel data of the fMIRI data; and
selecting at least one of the candidate parcellations according to their respective similarities.

4. The method of claim 1, further comprising:
generating (i) a training input comprising the channel data of the EEG data corresponding to the electrode and (ii) a ground-truth output identifying one or more parcellations whose brain activity was captured by the channel data of the EEG data corresponding to the electrode; and
training a machine learning model using the training input and the ground-truth output, wherein the machine learning model is configured to process first channel data captured by an electrode and to generate a prediction of a parcellation represented by the first channel data.

5. The method of claim 4, wherein the machine learning model comprises a recurrent neural network that processes an EEG time series captured by an electrode and generates a network output comprising, for each of a plurality of first parcellations, a value representing a likelihood that the EEG time series represents the first parcellation.

6. The method of claim 1, wherein the region of interest of each electrode is a sphere with a same radius.

7. A system comprising one or more computers and one or more storage devices storing instructions that are operable, when executed by the one or more computers, to cause the one or more computers to perform operations comprising:
obtaining brain data comprising:
EEG data captured from a brain of a subject, the EEG data comprising respective channel data corresponding to each of a plurality of electrodes of an EEG sensor, and
fMRI data captured from the brain of the subject, the fMRI data comprising respective voxel data corresponding to each of a plurality of voxels, wherein the voxel data of each voxel represents a respective region of a respective parcellation in the brain of the subject;
identifying, in a three-dimensional coordinate system, a respective location for each electrode of the plurality of electrodes;
generating, using the respective identified locations of each electrode of the plurality of electrodes, data representing a location in the three-dimensional coordinate system of each voxel of the plurality of voxels, the generating comprising:
identifying one or more particular voxels of the plurality of voxels that correspond to a reference electrode of the plurality of electrodes of the EEG sensor, the identifying comprising:
determining, from the fMRI data, a plurality of image slices, wherein each image slice represents the brain of the subject at a different elevation along a vertical axis of the three-dimensional coordinate system;
identifying a particular image slice that represents a topmost region of the brain of the subject by processing at least some of the plurality of image slices to generate respective binarized image slices, wherein each pixel of each binarized image slice has a value that identifies whether the pixel represents the brain of the subject or not; and determining the particular image slice to be a preceding image slice, along the vertical axis, before a first image slice that does not include any pixels representing the brain of the subject;

determining a center of mass of a set of pixels of the particular image slice, where the set of pixels have been determined to represent the brain of the subject; and determining the one or more particular voxels to include a voxel that includes the determined center of mass; and aligning, in the three-dimensional coordinate system, the one or more particular voxels and the reference electrode of the EEG sensor;

determining, for each electrode of the plurality of electrodes, a region of interest in the three-dimensional coordinate system, wherein the region of interest of each electrode is a sphere having a predetermined size; and identifying, for each electrode of the plurality of electrodes, one or more corresponding parcellations in the brain of the subject, wherein each parcellation that corresponds to an electrode at least partially overlaps with the region of interest of the electrode.

8. The system of claim 7, wherein identifying, for each electrode of the plurality of electrodes, one or more corresponding parcellations comprises:

identifying, from the plurality of voxels of the fMRI data, a plurality of first voxels whose location in the three-dimensional coordinate system overlaps with the region of interest of the electrode;

determining, for each first voxel, the parcellation that the first voxel represents; and identifying at least one parcellation that is represented by one or more respective first voxels overlapping with the electrode.

9. The system of claim 7, wherein identifying, for each electrode of the plurality of electrodes, one or more corresponding parcellations comprises:

identifying a plurality of candidate parcellations;

for each candidate parcellation, processing (i) the channel data of the EEG data corresponding to the electrode and (ii) the voxel data of the fMRI data corresponding to the candidate parcellation to determine a similarity between the channel data of the EEG data and the voxel data of the fMIRI data; and selecting at least one of the candidate parcellations according to their respective similarities.

10. The system of claim 7, the operations further comprising:

generating (i) a training input comprising the channel data of the EEG data corresponding to the electrode and (ii) a ground-truth output identifying one or more parcellations whose brain activity was captured by the channel data of the EEG data corresponding to the electrode; and training a machine learning model using the training input and the ground-truth output, wherein the machine learning model is configured to process first channel data captured by an electrode and to generate a prediction of a parcellation represented by the first channel data.

11. The system of claim 10, wherein the machine learning model comprises a recurrent neural network that processes an EEG time series captured by an electrode and generates a network output comprising, for each of a plurality of first parcellations, a value representing a likelihood that the EEG time series represents the first parcellation.

12. One or more non-transitory storage media storing instructions that when executed by one or more computers cause the one or more computers to perform operations comprising:

obtaining brain data comprising:

EEG data captured from a brain of a subject, the EEG data comprising respective channel data corresponding to each of a plurality of electrodes of an EEG sensor, and fMRI data captured from the brain of the subject, the fMRI data comprising respective voxel data corresponding to each of a plurality of voxels, wherein the voxel data of each voxel represents a respective region of a respective parcellation in the brain of the subject;

identifying, in a three-dimensional coordinate system, a respective location for each electrode of the plurality of electrodes;

generating, using the respective identified locations of each electrode of the plurality of electrodes, data representing a location in the three-dimensional coordinate system of each voxel of the plurality of voxels, the generating comprising:

identifying one or more particular voxels of the plurality of voxels that correspond to a reference electrode of the plurality of electrodes of the EEG sensor, the identifying comprising:

determining, from the fMRI data, a plurality of image slices, wherein each image slice represents the brain of the subject at a different elevation along a vertical axis of the three-dimensional coordinate system;

identifying a particular image slice that represents a topmost region of the brain of the subject by processing at least some of the plurality of image slices to generate respective binarized image slices, wherein each pixel of each binarized image slice has a value that identifies whether the pixel represents the brain of the subject or not; and determining the particular image slice to be a preceding image slice, along the vertical axis, before a first image slice that does not include any pixels representing the brain of the subject;

determining a center of mass of a set of pixels of the particular image slice, where the set of pixels have been determined to represent the brain of the subject; and determining the one or more particular voxels to include a voxel that includes the determined center of mass; and aligning, in the three-dimensional coordinate system, the one or more particular voxels and the reference electrode of the EEG sensor;

determining, for each electrode of the plurality of electrodes, a region of interest in the three-dimensional coordinate system, wherein the region of interest of each electrode is a sphere having a predetermined size; and identifying, for each electrode of the plurality of electrodes, one or more corresponding parcellations in the brain of the subject, wherein each parcellation that corresponds to an electrode at least partially overlaps with the region of interest of the electrode.

13. The non-transitory storage media of claim 12, wherein identifying, for each electrode of the plurality of electrodes, one or more corresponding parcellations comprises:

identifying, from the plurality of voxels of the fMRI data, a plurality of first voxels whose location in the three-dimensional coordinate system overlaps with the region of interest of the electrode;
determining, for each first voxel, the parcellation that the first voxel represents; and
identifying at least one parcellation that is represented by one or more respective first voxels overlapping with the electrode.

14. The non-transitory storage media of claim 12, wherein identifying, for each electrode of the plurality of electrodes, one or more corresponding parcellations comprises:
identifying a plurality of candidate parcellations;
for each candidate parcellation, processing (i) the channel data of the EEG data corresponding to the electrode and (ii) the voxel data of the fMRI data corresponding to the candidate parcellation to determine a similarity between the channel data of the EEG data and the voxel data of the fMRI data; and
selecting at least one of the candidate parcellations according to their respective similarities.

15. The non-transitory storage media of claim 12, the operations further comprising:
generating (i) a training input comprising the channel data of the EEG data corresponding to the electrode and (ii) a ground-truth output identifying one or more parcellations whose brain activity was captured by the channel data of the EEG data corresponding to the electrode; and
training a machine learning model using the training input and the ground-truth output, wherein the machine learning model is configured to process first channel data captured by an electrode and to generate a prediction of a parcellation represented by the first channel data.

16. The non-transitory storage media of claim 15, wherein the machine learning model comprises a recurrent neural network that processes an EEG time series captured by an electrode and generates a network output comprising, for each of a plurality of first parcellations, a value representing a likelihood that the EEG time series represents the first parcellation.

* * * * *